(12) United States Patent
Fukuura et al.

(10) Patent No.: US 10,533,971 B2
(45) Date of Patent: Jan. 14, 2020

(54) BIOSENSOR

(71) Applicant: KYOCERA CORPORATION, Kyoto (JP)

(72) Inventors: Atsuomi Fukuura, Seika-cho (JP); Toru Fukano, Seika-cho (JP); Yuji Kishida, Seika-cho (JP); Hiroyasu Tanaka, Seika-cho (JP); Hideharu Kurioka, Kizugawa (JP)

(73) Assignee: KYOCERA CORPORATION, Kyoto (JP)

(*) Notice: Subject to any disclaimer, the term of this patent is extended or adjusted under 35 U.S.C. 154(b) by 59 days.

(21) Appl. No.: 15/714,997

(22) Filed: Sep. 25, 2017

(65) Prior Publication Data
US 2018/0052139 A1    Feb. 22, 2018

Related U.S. Application Data

(63) Continuation of application No. 14/123,752, filed as application No. PCT/JP2012/069348 on Jul. 30, 2012, now Pat. No. 9,772,310.

(30) Foreign Application Priority Data

Jul. 28, 2011 (JP) ................................. 2011-165163
Mar. 23, 2012 (JP) ................................. 2012-067617

(51) Int. Cl.
*G01N 29/02* (2006.01)
*G01N 29/22* (2006.01)
*G01N 33/487* (2006.01)

(52) U.S. Cl.
CPC ........... *G01N 29/02* (2013.01); *G01N 29/022* (2013.01); *G01N 29/222* (2013.01);
(Continued)

(58) Field of Classification Search
CPC ................. G01N 29/02; G01N 29/222; G01N 2291/0255; G01N 33/48707
(Continued)

(56) References Cited

U.S. PATENT DOCUMENTS 4,598,224 A * 7/1986 Ballato ................ G01N 29/022
                                                        310/311
5,283,037 A * 2/1994 Baer ..................... G01N 29/022
                                                        310/311
(Continued)

FOREIGN PATENT DOCUMENTS

JP    02-227661 A    9/1990
JP    03-209157 A    9/1991
(Continued)

OTHER PUBLICATIONS

International Search Report under Patent Cooperation Treaty (PCT) for PCT/JP2012/069348, dated Oct. 4, 2012; 4 pages.

*Primary Examiner* — Daniel S Larkin
(74) *Attorney, Agent, or Firm* — Duane Morris LLP

(57) ABSTRACT

A biosensor, including: a first cover member comprising an element-accommodating recess in an upper face thereof; a detection element using a surface acoustic wave, the detection element including an element substrate accommodated in the element-accommodating recess, and at least one detection unit located on an upper face of the element substrate configured to perform detection of an analyte; and a second cover member joined to the first cover member and covering the detection element, and including an inflow port from which the analyte flows in and a groove which extends from the inflow port to at least above the at least one detection unit and constitutes a capillary.

17 Claims, 15 Drawing Sheets

(52) U.S. Cl.
CPC .......... *G01N 33/48707* (2013.01); *G01N 2291/0255* (2013.01); *G01N 2291/0256* (2013.01); *G01N 2291/0423* (2013.01)

(58) Field of Classification Search
USPC .............. 73/61.45, 61.49, 61.79, 64.53
See application file for complete search history.

(56) References Cited

U.S. PATENT DOCUMENTS

| | | | | |
|---|---|---|---|---|
| 6,310,421 B2* | 10/2001 | Morishima | ............ | H03H 9/059 310/313 R |
| 7,413,892 B2* | 8/2008 | Hunt | ............... | G01N 29/022 310/311 |
| 7,938,030 B2* | 5/2011 | Saiki | ............... | B01L 3/5027 422/503 |
| 2005/0226773 A1* | 10/2005 | Liu | ............... | G01N 29/022 422/68.1 |
| 2010/0031366 A1* | 2/2010 | Knight | ............... | G06Q 10/10 726/26 |

FOREIGN PATENT DOCUMENTS

| | | | | | |
|---|---|---|---|---|---|
| JP | 05-240762 | A | | 9/1993 | |
| JP | 2002-026675 | | * | 1/2002 | |
| JP | 2004-151016 | A | | 5/2004 | |
| JP | 2005-249491 | A | | 9/2005 | |
| JP | 2006-162318 | A | | 6/2006 | |
| JP | 2006-184011 | A | | 7/2006 | |
| JP | 2007-150824 | | * | 6/2007 | |
| JP | 2007-517221 | A | | 6/2007 | |
| JP | 2007-520698 | | | 7/2007 | |
| JP | 2010-239477 | A | | 10/2010 | |
| WO | WO-2004/061444 | A1 | | 7/2004 | |
| WO | WO-2005066621 | A1 | * | 7/2005 | ........... G01N 29/022 |
| WO | WO-2006/027945 | A1 | | 3/2006 | |

\* cited by examiner

BIOSENSOR

CROSS-REFERENCE TO RELATED APPLICATION

This application is a continuation application of U.S. patent application Ser. No. 14/123,752 filed Mar. 4, 2014 (now U.S. Pat. No. 9,772,310), which is a U.S. National Phase application PCT/JP2012/069348 filed Jul. 30, 2012, which claims priority to JP2012-067617 filed Mar. 23, 2012 and JP2011-165163 filed Jul. 28, 2011, all of which are incorporated by reference herein in their entireties

TECHNICAL FIELD

The present invention relates to a biosensor capable of performing measurement regarding properties of liquid analyte specimens or measurement regarding components included in the liquid.

BACKGROUND ART

There are known biosensors which use detection elements such as surface acoustic wave devices to perform measurement regarding properties of liquid analytes or measurement regarding components of the liquid (for example, see PTLs 1 through 3).

For example, a biosensor using a surface acoustic wave device is configured with a detection unit, which reacts with components included in analyte specimens, on a piezoelectric substrate. The properties or components of the liquid analyte are detected by measuring change in surface acoustic waves propagating through this detection unit. Measurement methods using surface acoustic wave devices and the like are advantageous over other measurement methods (the enzyme method, for example), in that multiple detection formats can be handled.

However, none of the conventional biosensors using detection elements such as surface acoustic wave devices have mechanisms to suction liquid themselves. This has necessitated, in order to feed the analyte to the detection unit, a task of first suctioning the specimen using equipment such as a micropipette and then feeding the suctioned specimen to the detection unit, which makes the procedures for measurement cumbersome. Also, the need for separate equipment increases the scale of the overall measurement apparatus.

On the other hand, there are known biosensors using a detection method different from that using detection elements such as surface acoustic wave devices. A reagent including an enzyme or the like is coated on a measurement electrode, the specimen is made to react with that portion, and change in current at the measurement electrode is read (see PTL 4).

PTL 4 discloses a technique in which the biosensor itself can suction specimens by capillary action. A slender specimen supply channel is extended to the portion of the measurement electrode where the reagent is coated and the specimen is suctioned to the portion electrode where the reagent is coated by capillary action.

Note that the method to measure specimens by coating the measurement electrode with a reagent including an enzyme or the like as in PTL 4 is limited in test items which can be measured, and accordingly is inconvenient in cases where testing of multiple items is desired.

Now, the structure of the measurement portion of the biosensor described in PTL 4 is one where a reagent is coated on the electrode, so the thickness of the measurement portion is that of the electrode, which is very thin. Accordingly, the slender specimen supply channel can be led up to the measurement portion without the specimen supply channel being blocked partway though.

On the other hand, detecting devices of biosensors using detection elements such as surface acoustic wave devices are formed using piezoelectric substrates or the like, so the detection element has a certain thickness. Accordingly, if the technique in PTL 4 is applied, the specimen supply channel will be blocked by the detection element, so feeding the specimen solution to the detection unit is difficult.

Accordingly, it has been found desirable to provide a biosensor including a suctioning mechanism, even in a case of using a thick detection element such as a surface acoustic wave device.

CITATION LIST

Patent Literature

PTL 1: Japanese Unexamined Patent Application Publication No. 5-240762
PTL 2: Japanese Unexamined Patent Application Publication No. 2006-184011
PTL 3: Japanese Unexamined Patent Application Publication No. 2010-239477
PTL 4: Japanese Unexamined Patent Application Publication No. 2005-249491

SUMMARY OF INVENTION

A biosensor according to one aspect of the present invention includes: a first cover member including an element-accommodating recess in an upper face thereof; a detection element including an element substrate accommodated in the element-accommodating recess, and at least one detection unit situated on the upper face of the element substrate to perform detection of an analyte; and a second cover member joined to the first cover and covering the detection element. The second cover member includes an inflow port from which the analyte flows in and a groove extending from the inflow port to at least above the detection unit.

A biosensor according to one aspect of the present invention includes: a mounting member including an inflow port into which an analyte flows in, at an end thereof, and a groove connected to the inflow port on an upper face thereof; a detection element including at least one detection unit situated on a principal face to perform detection of the analyte, mounted on the mounting member with the detection unit being situated above the groove in a state of the principal face facing the upper face of the mounting member; and a cover member including an element-accommodating recess on a lower face thereof. The cover member is joined to the mounting member and accommodates the detection element in the element-accommodating recess.

Also, a biosensor according to one aspect of the present invention includes: a cover member including an inflow port for an analyte, a groove-shaped channel connected to the inflow port, and a recessed space connected to the channel; and a detection element including a element substrate accommodated in the space, and a detection unit situated on an upper face of the element substrate and reacting with a component included in the analyte.

According to the biosensor, accommodating the detection element in the element-accommodating recess allows a channel of analyte solution to be secured from the inflow port to the detection unit, and analyte solution suctioned from the inflow port by capillary action or the like can be fed to the detection unit, even in a case of using a thick detection element. That is to say, a biosensor can be provided which is easy to use for measurement work, having a suctioning mechanism for analyte solution itself while using a thick detection element.

BRIEF DESCRIPTION OF DRAWINGS

FIG. 11(a) is a cross-sectional view corresponding to FIG. 4(a), and FIG. 11(b) is a cross-sectional view corresponding to FIG. 4(b).

FIG. 14(a) is a cross-sectional view of the portion corresponding to FIG. 4(a), and FIG. 14(b) is a cross-sectional view of the portion corresponding to FIG. 4(b).

FIG. 20(a) is a cross-sectional view of the portion corresponding to FIG. 4(a), and FIG. 20(b) is a cross-sectional view of the portion corresponding to FIG. 4(b).

DESCRIPTION OF EXEMPLARY EMBODIMENTS

Figure 1:
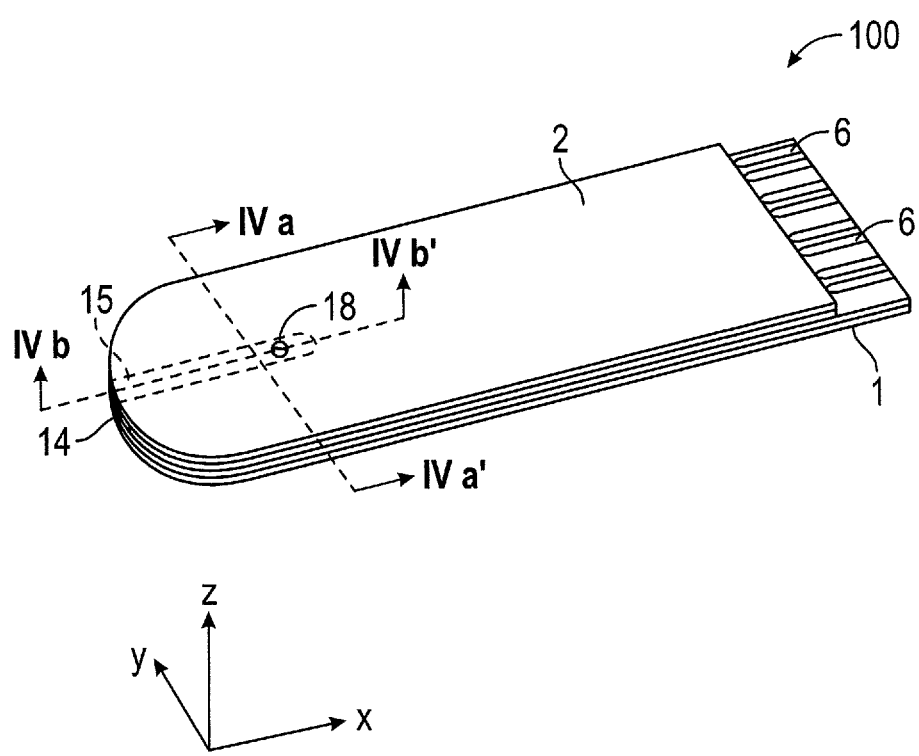
FIG. 1 is a perspective view of a biosensor according to a first embodiment of the present invention.

Embodiments of the biosensor according to the present invention will be described in detail with reference to the drawings. Note that components which are the same in the drawings described below are denoted with the same reference numerals. The sizes of the members and distances among the members are illustrated schematically, and may be different from actual sizes and distances.

Either side of the biosensor 100 may be up or down, but for sake of description in the following, an orthogonal coordinates system xyz is defined, and terms such as "upper face" and "lower face" are used with the positive side of the z direction being up.

First Embodiment

The biosensor 100 primarily includes a first cover member 1, a second cover member 2, and a detection element 3. The first cover member 1 includes a first board 1a and a second board 1b layered upon the first board 1a, and the second cover member 2 includes a third board 2a layered upon the second board 1b and a fourth board 2b layered upon the third board 2a. The detection element 3 is a surface acoustic wave device which primarily includes an element substrate 10, a first IDT (InterDigital Transducer) electrode 11, a second IDT electrode 12, and detection units 13 (see FIG. 5).

The first cover member 1 and second cover member 2 are applied to each other, and the detection element 3 is accommodated within the first cover member 1 and second cover member 2. The first cover member 1 has an element-accommodating recess 5 on the upper face thereof, with the detection element 3 situated in the element-accommodating recess 5, as illustrated in the cross-sectional views in FIG. 4.

The an inflow port 14, through which the specimen solution enters, is formed at the edge of the second cover member 2 in the longitudinal direction (x direction), as illustrated in FIG. 1. A groove 15 extending from the inflow port 14 toward a portion directly above the detection element 3 is also formed in the second cover member 2. The groove 15 is illustrated by dotted lines in FIG. 1 to indicate the position thereof.

Figure 2:
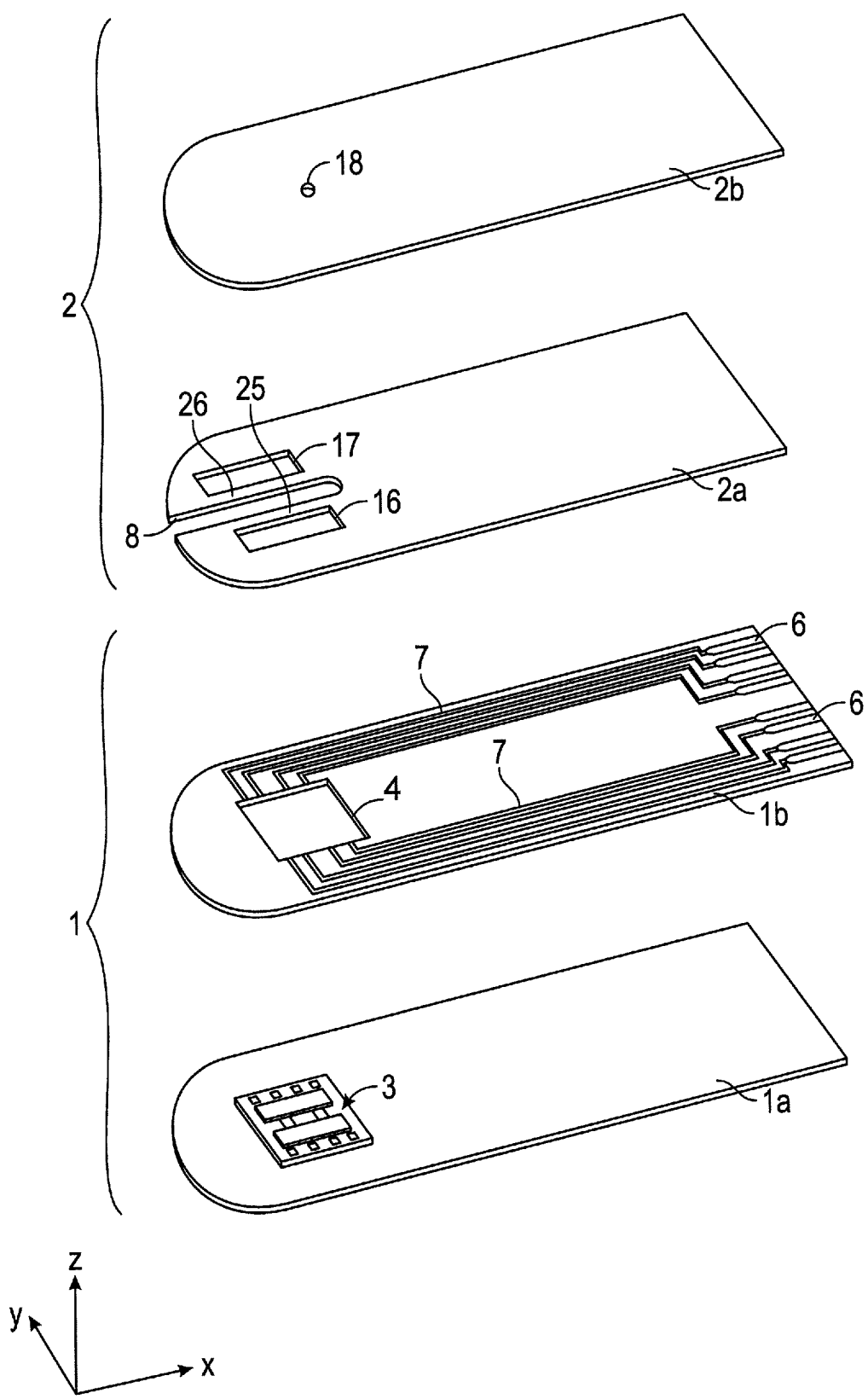
FIG. 2 is an exploded perspective view of a first cover member and a second cover member.

FIG. 2 illustrates an exploded perspective view of the first cover member 1 and second cover member 2.

The first board 1a included in the first cover member 1 is formed as a flat plate, 0.1 mm to 0.5 mm thick, for example. The planar shape of the first board 1a is generally rectangular, but one end in the longitudinal direction is an arc shape protruding outwards. The length of the first board 1a in the x direction is 1 cm to 5 cm, and the length in the y direction is 1 cm to 3 cm, for example.

The second board 1b is bonded onto the upper face of the first board 1a. The second board 1b is in the form of a flat plate frame, formed by a recess-forming through hole 4 having been formed in a flat plate frame form. The thickness thereof is 0.1 mm to 0.5 mm, for example. The outer form thereof in planar view is approximately the same as that of the first board 1a, and the x-directional length and y-directional length are also approximately the same as those of the first board 1a.

Joining the second board 1b to which the recess-forming through hole 4 has been formed, to the first board 1a, forms the element-accommodating recess 5 in the first cover member 1 of the flat plate form. That is to say, the upper face of the first board 1a situated within the recess-forming through hole 4 serves as the bottom face of the element-accommodating recess 5, and the inner walls of the recess-forming through hole 4 serve as the inner walls of the element-accommodating recess 5.

Terminals 6, and wiring 7 laid from the terminals 6 to the recess-forming through hole 4, are formed on the upper face of the second board 1b. The terminals 6 are formed at the other end of the second board 1b in the x direction on the upper face thereof. When the biosensor 100 is inserted into an external measurement instrument (not illustrated), the portion where the terminals 6 are formed is the portion actually inserted thereto. The terminals 6 are to be electrically connected to the external measurement instrument. Also, the terminals 6 and detection element 3 are electrically connected by the wiring 7 and so forth. Signals are input to the biosensor 100 from the external measurement instrument via the terminals 6, and signals from the biosensor 100 are output to the external measurement instrument via the terminals 6.

The second cover member 2 is joined to the upper face of the first cover member 1 made up of the first board 1a and second board 1b. The second cover member 2 includes the third board 2a and fourth board 2b.

The third board 2a is bonded to the upper face of the second board 1b. The third board 2a is formed as a flat plate, 0.1 mm to 0.5 mm thick, for example. The planar shape of the second board 2a is generally rectangular, but one end in the longitudinal direction is an arc shape protruding outwards, in the same way as with the first board 1a and second board 1b. The length of the third board 2a in the x direction is somewhat shorter than the length of the second board 1b in the x direction, 0.8 mm to 4.8 cm, for example, so that the terminals 6 on the second board 1b will be exposed. The length in the y direction is 1 cm to 3 cm, for example, the same as with the first board 1a and second board 1b.

A notch 8 is formed in the third board 2a. The notch 8 is a portion formed by notching out the third board 2a from the tip of the arc-shaped one end toward the other end in the x direction. The notch 8 penetrates the third board 2a in the thickness direction. This notch 8 is to form the groove 15. A first through hole 16 and a second through hole 17 which penetrate the third board 2a in the thickness direction are formed on either side of the notch 8 in the third board 2a. The arrangement is such that the connection portion between the detection element 3 and wiring 7 is situated within the first through hole 16 and second through hole 17 when layering the third board 2a on the second board 1b. The portion between the first through hole 16 and notch 8 of the third board 2a serves as a first partition 25 partitioning between the groove 15 and the space formed by the first through hole 16, which will be described later. Also, the portion between the second through hole 17 and notch 8 of the third board 2a serves as a second partition 26 partitioning between the groove 15 and the space formed by the second through hole 17.

The fourth board 2b is bonded onto the upper face of the third board 2a. The fourth board 2b is in the form of a flat plate, and the thickness thereof is 0.1 mm to 0.5 mm, for example. The outer form thereof in planar view is approximately the same as that of the third board 2a, and the x-directional length and y-directional length are also approximately the same as those of the third board 2a.

Bonding the fourth board 2b onto the third board 2a where the notch 8 has been formed forms the groove 15 on the lower face of the second cover member 2. That is to say, the lower face of the fourth board 2b situated within the notch 8 serves as the bottom face of the groove 15, and the inner walls of the notch 8 are the inner walls of the groove 15. The groove 15 extends from the inflow port 14 to at least a region directly above the detection units 13. The cross-sectional shape thereof is rectangular, for example.

A vent hole 18 penetrating the fourth board 2b in the thickness direction is formed in the fourth board 2b. The vent hole 18 is situated at the end portion of the notch 8 when the fourth board 2b is layered on the third board 2a. Accordingly, the end of the groove 15 is connected with the vent hole 18. This vent hole 18 serves to externally discharge air and the like that is in the groove 15.

The vent hole 18 may be of any shape, such as a cylinder, square pillar, or the like, as long as air within the channel can be removed. However, if the planar shape of the vent hole 18 is too great, the area of analyte solution field in the channel coming into contact with external air also increases, and moisture tends to evaporate from the analyte solution. This readily leads to change in concentration of the analyte solution, incurring deterioration in measurement precision. Accordingly, the planar shape of the vent hole 18 is made to be no larger than necessary. Specifically, in a case where the vent hole 18 is formed as a cylinder, the diameter is made to be 1 mm or smaller, and in a case where the vent hole 18 is formed as a square pillar, the length of each side is made to be 1 mm or smaller.

The inner walls of the vent hole 18 are hydrophobic. This prevents the analyte solution filling the channel from leaking out from the vent hole 18.

The first board 1a, second board 1b, third board 2a, and fourth board 2b are formed of paper, plastic, celluloid, ceramic, or the like, for example. These boards may all be formed of the same material. Forming the boards all of the same material enables the thermal expansion coefficients of the boards to be made approximately uniform, thereby suppressing deformation due to difference in thermal expansion coefficients among the boards. Also, the detection units 13 may be coated with biological materials, some of which are altered by external light such as ultraviolet rays. In this case, a non-transparent material having light-shielding properties is preferably used as the material for the first cover member 1 and second cover member 2. On the other hand, in cases where there is hardly any alteration at the detection units 13 due to external light, the second cover member 2 where the groove 15 is formed may be formed of a material close to transparent. This allows of visual inspection of the analyte solution flowing through the channel.

Figure 5:
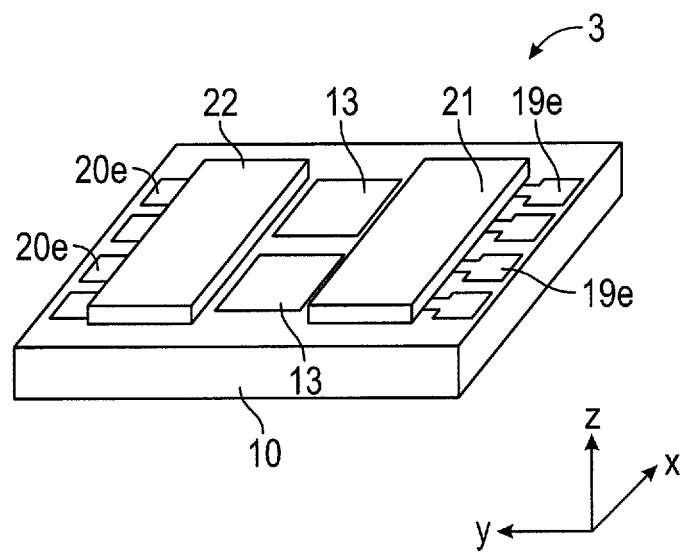
FIG. 5 is a perspective view of a detection element used in the biosensor illustrated in FIG. 1.

Next, the detection element 3 will be described in detail. FIG. 5 is a perspective view of the detection element 3, and FIG. 6 is a plan view of the detection element 3 in a state with a first protective member 21 and a second protective member 22 removed.

The detection element 3 includes the element substrate 10, and the detection units 13, first IDT electrodes 11, second IDT electrodes 12, and first extracting electrodes 19 and second extracting electrodes 20, disposed upon the upper face of the element substrate 10.

The element substrate 10 is a monocrystal substrate having piezoelectric properties, such as a lithium tantalite (LiTaO$_3$) monocrystal, a lithium niobate (LiNbO$_3$) monocrystal, or crystal, for example. The planar shape and dimensions of the element substrate 10 may be set as appropriate. One example of the thickness of the element substrate 10 is 0.3 mm to 1 mm.

Figure 6:
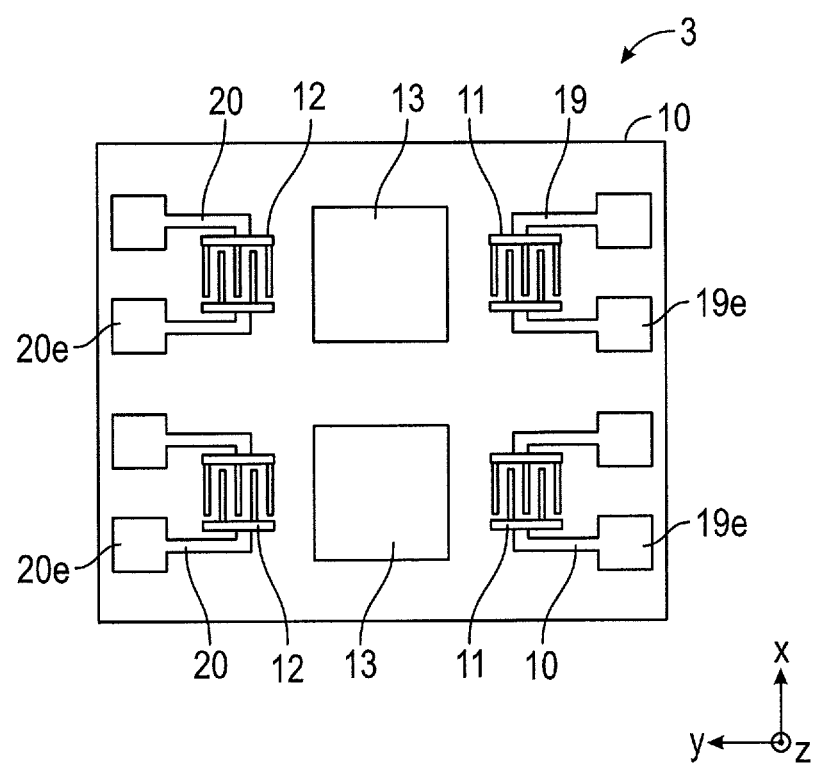
FIG. 6 is a plan view of the detection element illustrated in FIG. 5 in a state with a first protective member and a second protective member removed.

The first IDT electrodes 11 include a pair of toothcomb electrodes, as illustrated in FIG. 6. The toothcomb electrodes include two bus bars, and multiple electrode fingers extending from each bus bar towards the other bus bar. Each pair of toothcomb electrodes is situated such that the multiple electrode fingers mesh with each other. The second IDT electrodes 12 are also configured in the same way as the first IDT electrodes 11. The first IDT electrodes 11 and second IDT electrodes 12 make transversal IDT electrodes.

The first IDT electrodes 11 are for generating a predetermined surface acoustic wave (SAW), and the second IDT electrodes 12 are for receiving the SAWs generated at the first IDT electrodes 11. The first IDT electrodes 11 and second IDT electrodes 12 are disposed on the same straight line so that SAWs generated at the first IDT electrodes 11 can be received at the second IDT electrodes 12. Frequency properties can be designed using parameters such as the number of electrode fingers of the first IDT electrodes 11 and second IDT electrodes 12, distance between adjacent electrode fingers, intersection width of the electrode fingers, and so forth. While there are various vibration modes for SAWs excited by the IDT electrodes, The detection element 3 employs a vibration mode of transverse waves called SH waves, for example.

Also, an elastic material may be provided to the outer side of the first IDT electrodes 11 and second IDT electrodes 12 in the direction of propagation of SAWs (y direction), to suppress reflection of the SAWs. The SAW frequency can be set within a range of several megahertz (MHz) to several gigahertz (GHz). Particularly, setting the SAW frequency to several hundred MHz to 2 GHz is practical, and enables reduction in size of the detection element 3 to be realized, thereby realizing reduction in size of the biosensor 100.

The first IDT electrodes 11 are connected with first extracting electrodes 19. The first extracting electrodes 19 are extracted from the first IDT electrodes 11 in the direction opposite to the detection units 13, and ends 19e of the first extracting electrodes 19 are electrically connected with the wiring 7 on the first cover member 1. The second IDT electrodes 12 are similarly connected with second extracting electrodes 20. The second extracting electrodes 20 are extracted from the second IDT electrodes 12 in the direction opposite to the detection units 13, and ends 20e of the second extracting electrodes 20 are electrically connected with the wiring 7.

The first IDT electrodes 11, second IDT electrodes 12, first extracting electrodes 19, and second extracting electrodes 20, are made of aluminum, an alloy of aluminum and copper, or the like, for example. These electrodes may be of a multi-layer structure. In a case of employing a multi-layer structure, the first layer is made of titanium or chromium, and the second layer is of aluminum or aluminum alloy, for example.

The first IDT electrodes 11 and second IDT electrodes 12 are covered by a protective film (not illustrated). The protective film is to contribute to prevention of oxidization of the first IDT electrodes 11 and second IDT electrodes 12. The protective film is formed of, for example, silicon oxide, aluminum oxide, zinc oxide, titanium oxide, silicon nitride, or silicon. The thickness of the protective film is, for example, around 1/10 of the thickness of the first IDT electrodes 11 and second IDT electrodes 12 (10 to 30 nm).

The protective film may be formed over the entire upper face of the element substrate 10, leaving the ends 19e of the first extracting electrodes 19 and the ends 20e of the second extracting electrodes 20 exposed.

The detection units 13 are situated between the first IDT electrodes 11 and second IDT electrodes 12. The detection units 13 are formed of, for example, metal film, and an aptamer made up of a nucleic acid or peptide fixed to the surface of the metal film. The metal film has a two-layered structure of chromium and a gold film formed on the chromium, for example. The detection units 13 are for causing a reaction with the target matter in the analyte solution. Specifically, upon the analyte solution coming into contact with the detection units 13, a particular target matter within the analyte solution binds to the aptamer corresponding to that target matter.

Taking a first IDT electrode, second IDT electrode, and detection unit 13, disposed in the y direction as one set, the biosensor 100 includes two of these sets. Thus, two types of detection can be performed with a single biosensor, by making the target matter reacting at one detection unit 13 to be different from the target matter reacting at the other detection unit 13.

Figure 4A:
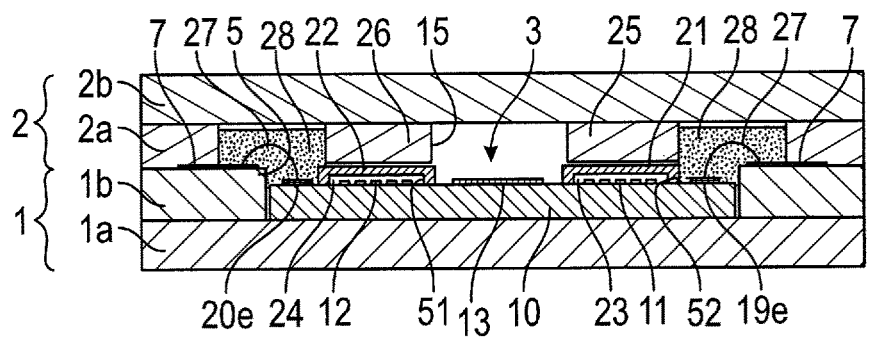
FIG. 4(a) is a cross-sectional view along IVa-IVa' in FIG. 1.
Figure 4B:
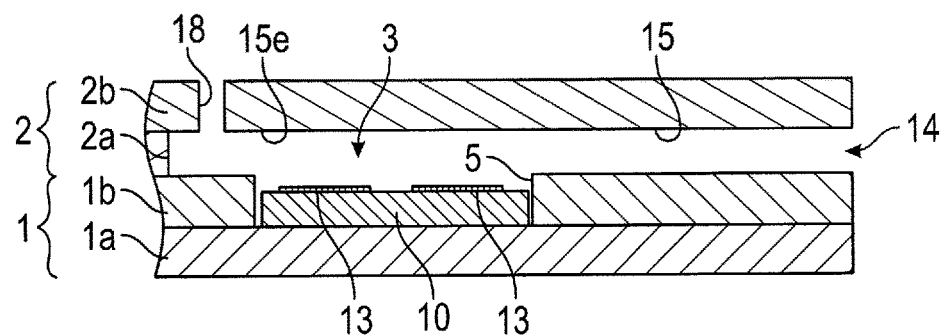
FIG. 4(b) is a cross-sectional view along IVb-IVb' in FIG. 1.

The first IDT electrodes 11 are covered by the first protective member 21 as illustrated in FIG. 5. The first protective member 21 is situated on the upper face of the element substrate 10, and has a first recess 51 opening toward the upward face side of the element substrate 10, as illustrated in FIG. 4(a). A region surrounded by the inner face of the first recess 51 and the upper face of the element substrate 10 in a state of the first protective member 21 being placed on the upper face of the element substrate 10 is a first vibration space 23. The first IDT electrodes 11 are sealed within the first vibration space 23. Accordingly, the first IDT electrodes 11 are, isolated from the external air and analyte solution, and thus the first IDT electrodes 11 can be protected. Also, deterioration of properties of the SAWs excited by the first IDT electrodes 11 can be suppressed by securing the first vibration space 23.

Similarly, the second IDT electrode 12 are covered by the second protective member 22. The second protective member 22 is situated on the upper face of the element substrate 10, and has a second recess 52 opening toward the upward face side of the element substrate 10, as illustrated in FIG. 4(a). A region surrounded by the inner face of the second recess 52 and the upper face of the element substrate 10 in a state of the second protective member 22 being placed on the upper face of the element substrate 10 is a second vibration space 24. The second IDT electrodes 12 are sealed within the second vibration space 24. Accordingly, the second IDT electrodes 12 are isolated from the external air and analyte solution, and thus the second IDT electrodes 12 can be protected. Also, deterioration of properties of the SAWs received by the second IDT electrode 12 can be suppressed by securing the second vibration space 24.

The first protective member 21 includes a ring-shaped frame fixed on the upper face of the element substrate 10 so as to surround the two first IDT electrodes 11 disposed in the x direction, and a lid fixed to the frame so as to seal the opening of the frame. This sort of structure can be formed by, for example, forming a resin film using photosensitive resin material and patterning this resin film by photolithography or the like. The second protective member 21 can also be formed in the same way.

Note that one first protective member 23 is covering two first IDT electrodes 11 in the biosensor 100, but an arrangement may be made where the two first IDT electrodes 11 are each covered by individual first protective members 23. Alternatively, the two first IDT electrodes 11 may be covered with one first protective member 23, and a partition disposed between the two first IDT electrodes 11. Similarly in the case of the second IDT electrodes 12, two second IDT electrodes 12 may be each covered by individual second protective members 24, or one second vibration space 24 may be used and a partition disposed between the two second IDT electrodes 12.

Detection of a analyte solution at the detection elements 3 using SAWs is performed as follows. First, a predetermined voltage is applied to the first IDT electrodes 11 from an external measuring instrument, via the wiring 7, first extracting electrodes 19, and so forth. The surface of the element substrate 10 is thus excited in the formation region of the first IDT electrodes 11, and a SAW having a predetermined frequency is generated. A part of the generated SAW is propagated toward the detection unit 13, passes through the detection unit 13, and then reaches the second IDT electrode 12. At the detection unit 13, the aptamer of the detection unit 13 has bound to the particular target matter in the analyte solution, so the weight of the detection unit 13 has increased by an amount equivalent to the amount of binding. Accordingly, properties of the SAW passing underneath the detection unit 13, such as phase, change. The SAW of which the properties have changed reach the second IDT electrode, whereupon corresponding voltage is generated at the second IDT electrode. This voltage is externally output via the second extracting electrode 20, wiring 7, and so forth, and read at the external measurement instrument, whereby the properties and components of the analyte solution can be found.

The biosensor 100 employs capillary action to guide the analyte solution to the detection unit 13. Specifically, joining the second cover member 2 to the first cover member 1 makes the portion of the groove 15 on the lower face of the second cover member 2 to become a slender tube. Capillary action can thus be made to occur at the slender tube formed by the groove 15, by setting the width, diameter, or the like of the groove 15 to predetermined values, taking into consideration the type of analyte solution, the material of the first cover member 1 and second cover member 2, and so forth. The width of the groove 15 (y-dimensional dimension) is, for example, 0.5 mm to 3 mm, and the depth (z-directional dimension) is, for example, 0.1 mm to 0.5 mm. The groove 15 also includes an extended portion 15e which extends beyond the detection unit 13. The second cover member 2 includes the vent hole 18 which is connected to the extended portion 15e. When the analyte solution enters the channel, air which had been present in the channel is vented out from the vent hole 18.

The tube which exhibits such capillary action is formed by the cover members first cover member 1 and second cover member 2. Thus, when the inflow port 14 is brought into contact with the analyte solution, the analyte solution is suctioned into within the cover members with the groove 15 as a channel. Accordingly, the biosensor 100 itself has a analyte solution suctioning mechanism, so suctioning of analyte solution can be performed without using an instrument such as a pipette. Also, the portion where the inflow port 14 is formed is rounded and the inflow port 14 is formed at the tip thereof, so the inflow port 14 can be readily discerned.

Part or all of the inner face of the channel of the biosensor 100, for example the bottom face of the groove 15, the walls of the groove 15, and so forth, are hydrophilic. Hydrophilic inner faces of the channel facilitate capillary action, so the analyte solution is more readily suctioned from the inflow port 14. The portion of the inner faces of the channel which are hydrophilic have an angle of contact of 60° or less as to water. An angle of contact of 60° or less causes capillary action more readily, and suction of the analyte solution into the inflow port occurs in a more sure manner when bringing the analyte solution into contact with the inflow port.

Conceivable methods to render the inner faces of the groove 15 hydrophilic include a method of subjecting the inner faces of the groove 15 to hydrophilicity induction processing, a method of applying a hydrophilic film on the inner faces of the groove 15, a method of forming the second cover member 2 configuring the groove 15 of a hydrophilic material, and so forth.

Of these, the method of subjecting the inner faces of the groove 15 to hydrophilicity induction processing, and the method of applying a hydrophilic film on the inner faces of the groove 15 cause the analyte solution to flow through the channel following the hydrophilic portions. Accordingly, almost all of the analyte solution flows through the channel, and flow of the analyte solution to unintended portions is suppressed, so highly precise measurement can be realized. Also, capillary action can be caused with these methods even if the cover members are formed of hydrophobic material. This is advantageous in that there are more options of materials which can be selected for the cover members.

The inner faces of the groove 15 may be subjected to hydrophilicity induction processing by, for example, asking the inner faces of the groove 15 by oxygen plasma, then coating with a silane coupling agent, and finally coupling with polyethylene glycol. Alternatively, the surface of inner faces of the groove 15 may be treated using a treatment agent including phosphorylcholine.

Figure 9A:
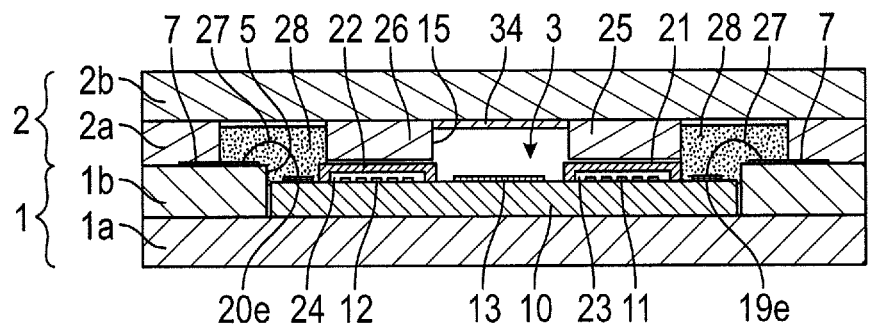
FIGS. 9(a), 9(b) and 9(c) are cross-sectional views illustrating an example of a biosensor where a hydrophilic film has been attached to a channel.
Figure 9B:
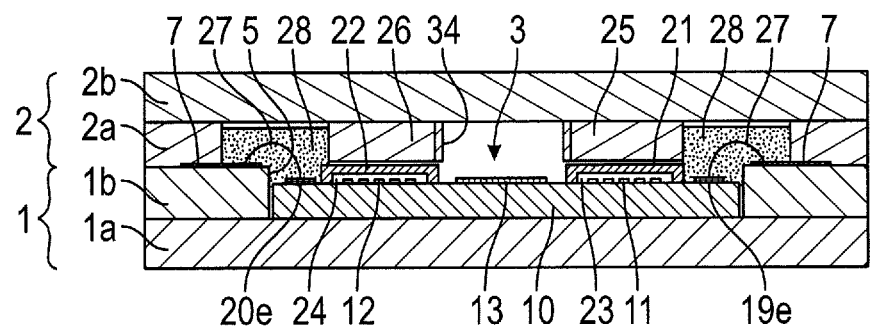
Figure 9C:
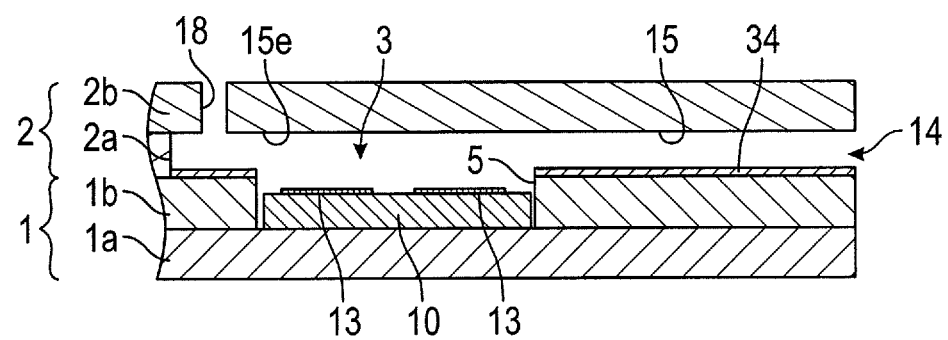

Also, a commercially-available polyester film or polyethylene film treated by hydrophilicity induction processing, or the like, may be used as the hydrophilic film. FIG. 9 illustrates examples of a hydrophilic film 34 applied to the channel. FIG. 9(a) and FIG. 9(b) are cross-sectional views corresponding to FIG. 4(a), and FIG. 9(c) is a cross-sectional view corresponding to FIG. 4(b). The film 34 may be formed to just the upper face of the channel, that is the bottom face of the groove 15, as illustrated in FIG. 9(a), or may be formed to just the side faces of the channel, that is the walls of the groove 15, as illustrated in FIG. 9(b). Alternatively, the film 34 may be formed to the lower face of the channel as illustrated in FIG. 9(c), or a combination of these FIG. 9(a) through FIG. 9(c) may be used.

Now, the depth of the analyte solution channel formed by the groove 15 is around 0.3 mm, and the thickness of the detection element 3 is around 0.3 mm, so the depth of the channel and the thickness of the detection element 3 are approximately equal. Accordingly, placing the detection element 3 on the channel in the state blocks off the channel. Thus, the biosensor 100 includes an element-accommodating recess 5 on the first cover member 1 where the detection element 3 is mounted, and the detection element 3 is stored in this element-accommodating recess 5, so as to prevent the analyte solution channel from being blocked, as illustrated in FIG. 4. That is, the depth of the element-accommodating recess 5 is made to be around the same as the thickness of the detection element 3, and the detection element 3 is mounted within the element-accommodating recess 5, thereby securing the channel formed by the groove 15.

Figure 3:
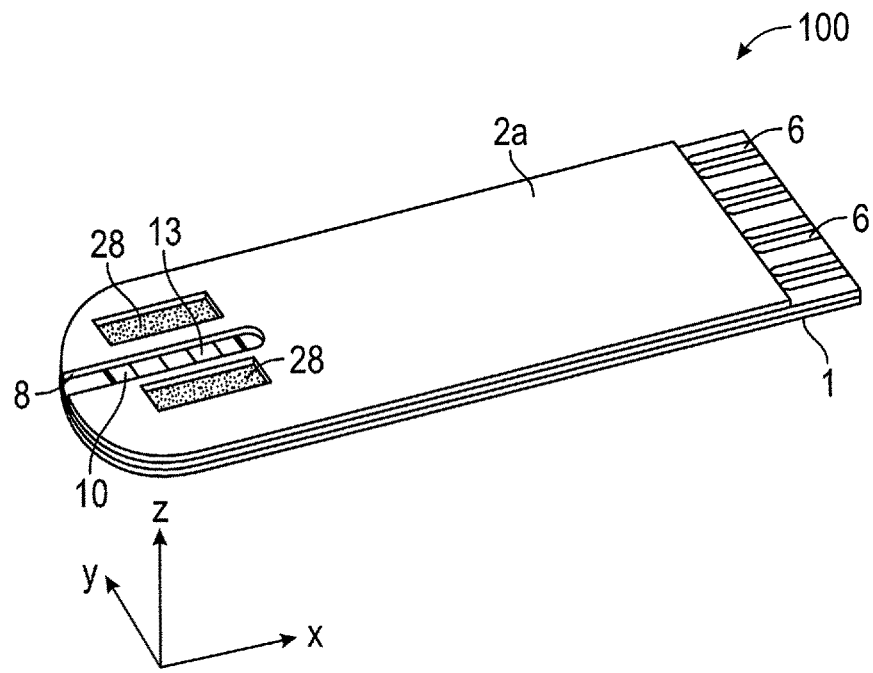
FIG. 3 is a perspective view of the biosensor illustrated in FIG. 1, in a state of a fourth board removed.

FIG. 3 is a perspective view illustrating a state where the fourth board 2b of the second cover member 2 has been removed. The analyte solution channel is secured, so the analyte solution flowing into the channel by capillary action can be smoothly guided to the detection unit 13.

The height of the upper face of the element substrate 10 from the bottom face of the element-accommodating recess 5 is preferably the same or smaller (lower) than the depth of the element-accommodating recess 5 as illustrated in FIG. 4, from the perspective of sufficiently securing the analyte solution channel. For example, an arrangement where the height of the upper face of the element substrate 10 from the bottom face of the element-accommodating recess 5 and the depth of the element-accommodating recess 5 are the same enables the bottom face of the channel and the detection unit 13 to be on approximately the same height, when viewing the inside of the groove 15 from the inflow port 14. The biosensor 100 is arranged such that the thickness of the element substrate 10 is smaller (thinner) than the depth of the element-accommodating recess 5, so that the height of the upper faces of the first protective member 21 and second protective member 22 from the bottom face of the element-accommodating recess 5 is approximately the same as the depth of the element-accommodating recess 5. If the height of the first protective member 21 and second protective member 22 from the bottom face of the element-accommodating recess 5 is greater (higher) than the depth of the element-accommodating recess 5, the first partition 25 and second partition 26 of the third board 2*a* will have to be worked so as to be thinner than the other portions. However, arranging so that the height of the first protective member 21 and second protective member 22 from the bottom face of the element-accommodating recess 5 is approximately the same as the depth of the element-accommodating recess 5 does away with the need for such working, facilitating production efficiency.

The planar shape of the element-accommodating recess 5 is, for example, a similar shape to the planar shape of the element substrate 10, and the element-accommodating recess 5 is somewhat larger than the element substrate 10. Specifically, the size of the element-accommodating recess 5 is such that when the element substrate 10 is mounted to the element-accommodating recess 5, there is formed a gap of around 100 μm between the side faces of the element substrate 10 and the inner walls of the element-accommodating recess 5.

The detection element 3 is fixed to the bottom face of the element-accommodating recess 5 by a die bond including, for example, epoxy resin, polyimide resin, silicon resin, or the like, as a primary component thereof. The ends 19*e* of the first extracting electrodes 19 and the wiring 7 are electrically connected by fine metal wires 27 formed of Au or the like, for example. This is the same for the connection between the ends 20*e* of the second extracting electrodes 20 and the wiring 7. Note that the connection of the first extracting electrodes 19 and second extracting electrodes 20 to the wiring 7 is not restricted to connection by the fine metal wires 27, and an electroconductive adhesive agent such as Ag paste or the like may be used, for example.

Spaces are formed at the connection portion of the first extracting electrodes 19 and second extracting electrodes 20 to the wiring 7 so damage to the fine metal wires 27 at the time of bonding the second cover member 2 to the first cover member 1 is suppressed. These spaces can be easily formed by forming the first through hole 16 and second through hole 17 in the third board 2*a* beforehand. The existence of the first partition 25 between the first through hole 16 and the groove 15 can suppress the analyte solution flowing through the groove 15 from flowing into the spaces formed by the first through hole 16. Accordingly, short-circuiting between the multiple first extracting electrodes 19 due to the analyte solution can be suppressed. In the same way, the existence of the second partition 26 between the second through hole 17 and the groove 15 can suppress the analyte solution flowing through the groove 15 from flowing into the spaces formed by the second through hole 17. Accordingly, short-circuiting between the multiple second extracting electrode 20 due to the analyte solution can be suppressed.

The first partition 25 is situated above the first protective member 21, and the second partition 26 is situated above the second protective member 22. Accordingly, the analyte solution channel is defined by not only the groove 15 but also by the side walls of the first protective member 21 and the side walls of the second protective member 22. From the perspective of preventing leakage of the analyte solution to the spaces formed by the first through hole 16 and second through hole 17, the first partition 25 preferably comes into contact with the upper face of the first protective member 21 and the second partition 26 with the upper face of the first protective member 22. However, the biosensor 100 is configured such that gaps are formed between the lower face of the first partition 25 and upper face of the first protective member 21, and between the lower face of the second partition 26 and the upper face of the second protective member 22. The gap is 10 μm to 60 μm, for example. Providing these gaps enables pressure applied to this portion when gripping the biosensor 100 between fingers to by absorbed at the gaps, thereby suppressing pressure from being directly applied to the first protective member 21 and second protective member 22. As a result, the first vibration space 23 and second vibration space 24 can be kept from greatly deforming. Also, analyte solutions normally have a certain level of viscoelasticity, so forming the gaps to be 10 μm to 60 μm makes it difficult for the analyte solution to enter the gaps, and leakage of the analyte solution to the gaps formed by the first through hole 16 and second through hole 17 can be suppressed.

The width of the first partition 25 is formed wider than the width of the first vibration space 23. In other words, the side wall of the first partition 25 is situated on the frame of the first protective member 21. Accordingly, even in a case where the first partition 25 comes into contact with the first hollow portion 21 due to external pressure, the first partition 25 is supported by the frame, so deformation of the first protective member 21 can be suppressed. Due to the same reason, the width of the second partition 26 is also preferably wider than the width of the first vibration space 25.

The first extracting electrodes 19, second extracting electrodes 20, fine metal wires 27, and wiring 7, within the spaces formed by the first through hole 16 and second through hole 17, are covered by an insulating member 28. Covering the first extracting electrodes 19, second extracting electrodes 20, fine metal wires 27, and wiring 7 by the insulating member 28 can suppress corrosion of these electrodes and the like. Also, providing the insulating member 27 enables the analyte solution to be held back by the insulating member 27 even if the analyte solution does enter into the gap between the first partition 25 and first protective member 21 or the gap between the second partition 26 and second protective member 22. Thus, short-circuiting between extracting electrodes due to leaking analyte solution can be suppressed.

Thus, according to the biosensor 100, the analyte solution channel from the inflow port 14 to the detection units 13 can be secured due to having accommodated the detection element 3 in the element-accommodating recess 5 in the first cover member 1, and the analyte solution suctioned by capillary action and so forth from the inflow port can be fed to the detection units 13. That is to say, a biosensor 100 including a suction mechanism in itself, and which uses a thick detection element 3, can be provided.

Figure 7:
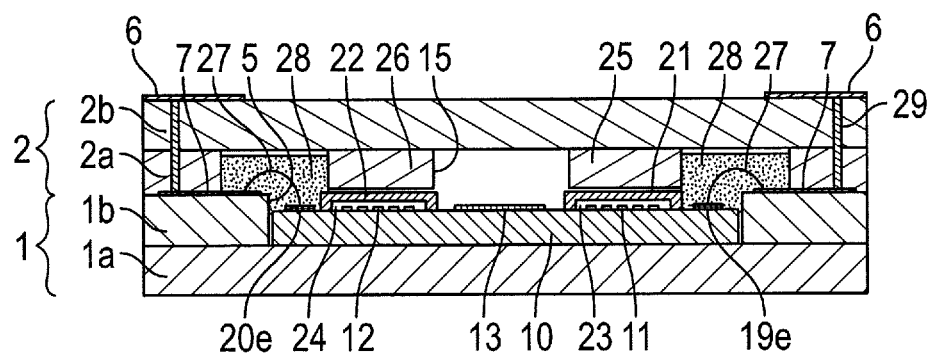
FIG. 7 is a cross-sectional view illustrating a modification of a biosensor according to an embodiment of the present invention.

FIG. 7 is a cross-sectional view illustrating a modification of the biosensor 100. This cross-sectional view corresponds to the cross-section in FIG. 4(a).

The position where the terminals 6 are formed has been changed with this modification. While the terminals 6 are formed at the other end of the second board 1b in the longitudinal direction in the above-described embodiment, the terminals 6 are formed on the upper face of the fourth board 2b in this modification. The terminals 6 and wiring 7 are electrically connected by through conductors 29 penetrating the second cover member 2. The through conductors 29 are formed of Ag paste, plating, or the like, for example. The terminals 6 may also be formed on the lower face side of the first cover member 1. Accordingly, the terminals 6 can be formed at optional positions on the first cover member 1 and second cover member 2, and the positions can be decided in accordance with the measurement instrument being used.

Figure 8:
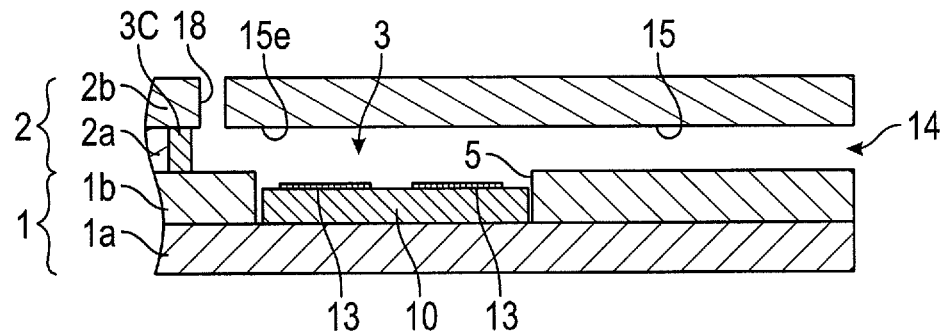
FIG. 8 is a cross-sectional view illustrating another modification of a biosensor according to an embodiment of the present invention.

FIG. 8 is a cross-sectional view illustrating another modification of the biosensor 100. This cross-sectional view corresponds to the cross-section in FIG. 4(b).

This modification includes a suctioning member 30 to suction the analyte solution at a predetermined speed. The suctioning member 30 is provided at the far end of the channel formed by the groove 15. This suctioning member 30 suctions excess analyte solution and makes the amount of analyte solution flowing over the detection unit 13 to be constant, so stable measurement can be performed. The suctioning member 30 is formed of a porous material such as sponge which can suction liquid, for example.

Second Embodiment

Figure 10:
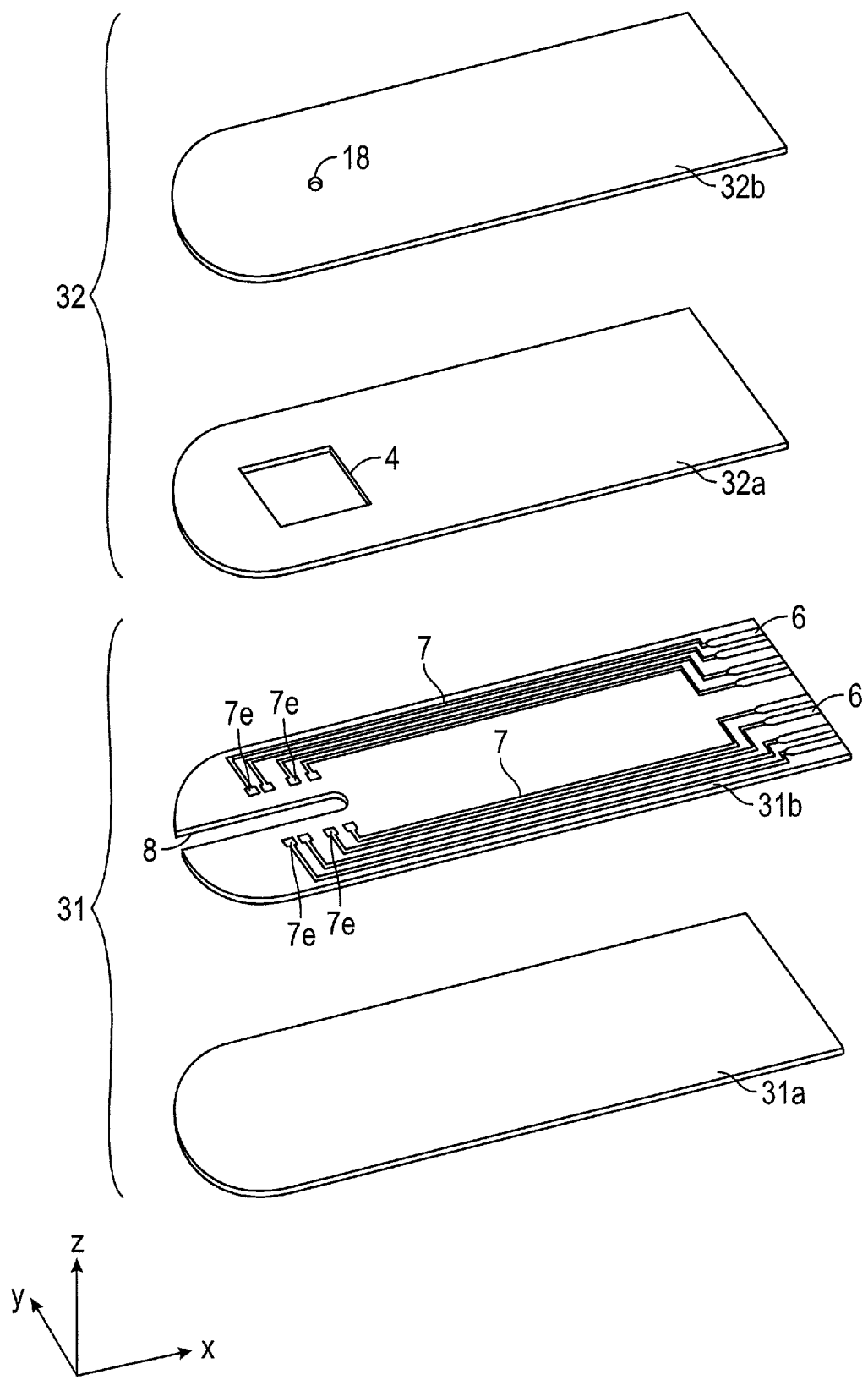
FIG. 10 is an exploded perspective view of a mounting member and cover member used in a biosensor according to a second embodiment of the present invention.
Figure 11A:
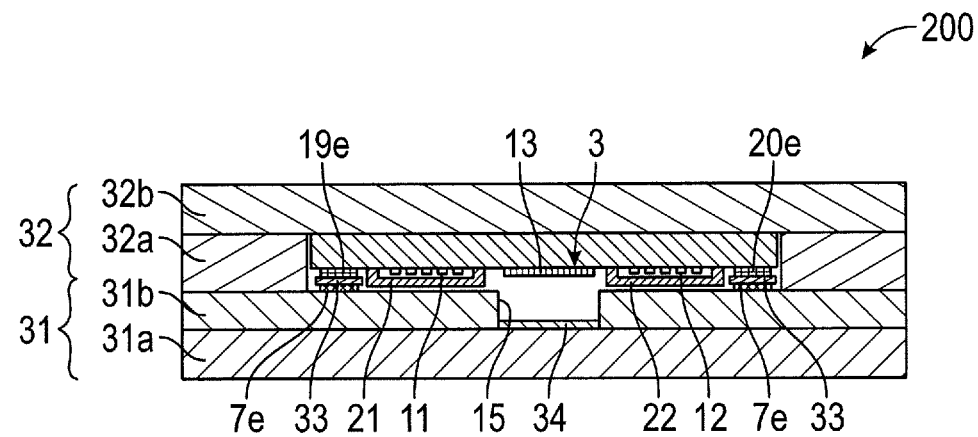
FIGS. 11(a) and 11(b) are cross-sectional views of the biosensor according to the second embodiment, where
Figure 11B:
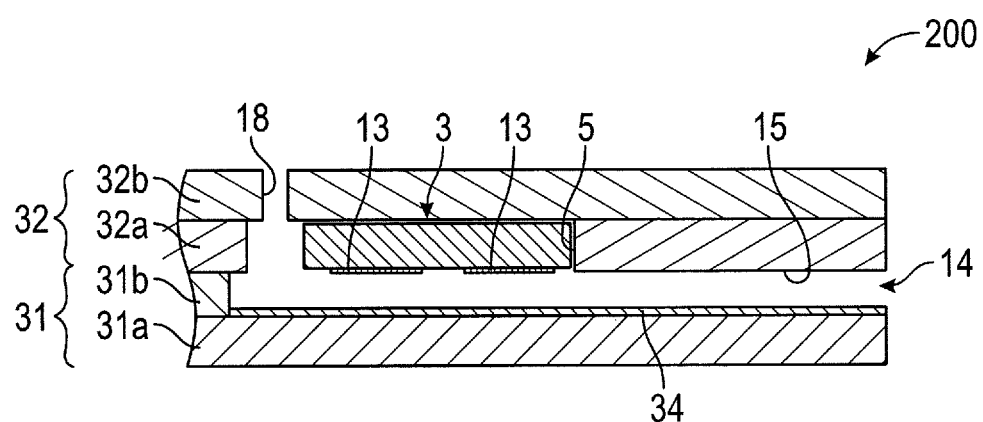

Next, a biosensor 200 according to a second embodiment will be described with reference to FIG. 10 and FIG. 11. FIG. 10 is an exploded perspective view of a mounting member 31 and a cover member 32 used in the biosensor 200. FIG. 11 is a cross-sectional view, with FIG. 11(a) and FIG. 11(b) being cross-sections corresponding to FIG. 4(a) and FIG. 4(b), respectively.

The biosensor 200 differs from the biosensor 100 according to the first embodiment described above primarily with regard to the form of the cover member and the method of mounting the detection element 3.

Specifically, the lower face of the detection element 3 is mounted to the first cover member 1 with the face of the detection element 3 on which the detection units 13 and first and second IDT electrodes 11 and 12 are formed facing upwards (z direction) in the biosensor 100 according to the first embodiment. On the other hand, the detection element 3 is mounted to the mounting member 31 with the face on which the detection units 13 and first and second IDT electrodes 11 and 12 are formed facing downwards (−z direction) in the biosensor 200. That is to say, the detection element 3 of the biosensor 200 is mounted face down.

The detection element 3 can be mounted face down by, for example, joining the ends 19e of the first extracting electrodes 19 on the element substrate 3 to ends 7e of the wiring 7 on the mounting member 31 by an electroconductive joining material 33 such as solder, and similarly joining the ends 20e of the second extracting electrodes 20 on the element substrate 3 to ends 7e of the wiring 7 on the mounting member 31 by the electroconductive joining material 33 such as solder. Joining may also be performed by electroconductive bumps of Au or the like, for example, besides such a joining method using solder.

In the face-up mounting of the detection element 3 as with the biosensor 100 according to the first embodiment, mechanical connection between the detection element 3 and the first cover member 1 is performed by the die bond material introduced between the lower face of the element substrate 3 and the element-accommodating recess, and electrical connection between the element substrate 3 and the first cover member 1 is performed by the fine metal wires 27. That is to say, mechanical connection and electrical joining are performed separately.

On the other hand, face-down mounting of the detection element 3 as with the biosensor 200 enables mechanical joining and electrical joining of the detection element 3 and mounting member 31 to be performed at the same time, so manufacturing efficiency is good.

The shape of the cover member of the biosensor 200 differs from that of the biosensor 100 according to the first embodiment as well. The biosensor 100 according to the first embodiment is configured such that, of the first cover member 1 and second cover member 2, the first cover member 1 which is disposed below is provided with the element-accommodating recess 5, and the detection element 3 is accommodated in this element-accommodating recess 5. Thus, the channel is guided to the detection units 13 without being blocked off by the detection element 3. Conversely, with the biosensor 200 as illustrated in FIG. 11, the element-accommodating recess 5 is provided to, of the mounting member 31 and cover member 32, the lower face of the cover member 1 disposed above, so that the detection element 3 is accommodated in this element-accommodating recess 5. Accordingly, a channel guided to the region below the detection units 13 can be secured while accommodating the thick detection element 3 within a cover member.

The mounting member 31 includes a fifth board 31a and sixth board 31b, and the cover member 32 includes a seventh board 32a and eighth board 32b, as illustrated in FIG. 10.

The fifth board 31a is formed as a flat plate, and basically is the same as the first board 1a according to the first embodiment. On the other hand, the sixth board 31b to be bonded to the fifth board 31b is different from the second board 1b according to the first embodiment, a notch 8 being formed thereto. Layering the sixth board 31b to which the notch 8 has been formed in this way on the plate-shaped fifth board 31a forms the fifth cover member 31 including an inflow port at one end and a groove 15 extending from the inflow port.

A recess-forming through hole 4 is formed to, of the seventh board 32a and eighth board 32b making up the cover member 32, the seventh board 32a disposed below. Layering the eighth board 32b on the upper face of the seventh board 32 to which the recess-forming through hole 4 has been formed, forms the cover member 32 with the element-accommodating recess 5 on the lower face. Note that the eighth board 32b is basically the same as the fourth board 2b according to the first embodiment.

Also, the biosensor 200 includes a hydrophilic film 34 on the bottom face of the groove 5, as illustrated in FIG. 11. On the other hand, the sixth board 31 is formed of a hydrophobic material. Accordingly, the analyte solution basically flows into the channel formed of the groove 5, and the analyte solution does not readily enter into the gap between the first protective member 21 and the upper face of the sixth board 31 and the gap between the second protective member 22 and the upper face of the sixth board 31. Accordingly, short-circuiting among ends 19e of the first extracting electrodes 19 and so forth by the analyte solution is suppressed.

Third Embodiment

Next, a biosensor 300 according to a third embodiment will be described with reference to FIG. 12 through FIG. 15.

The biosensor 300 differs from the biosensor 100 according to the above-described first embodiment with regard to the point of including an assisting board 35 and to the structure of the portion forming the first vibration space 23 and second vibration space 24 of the detecting element 3.

Figure 12:
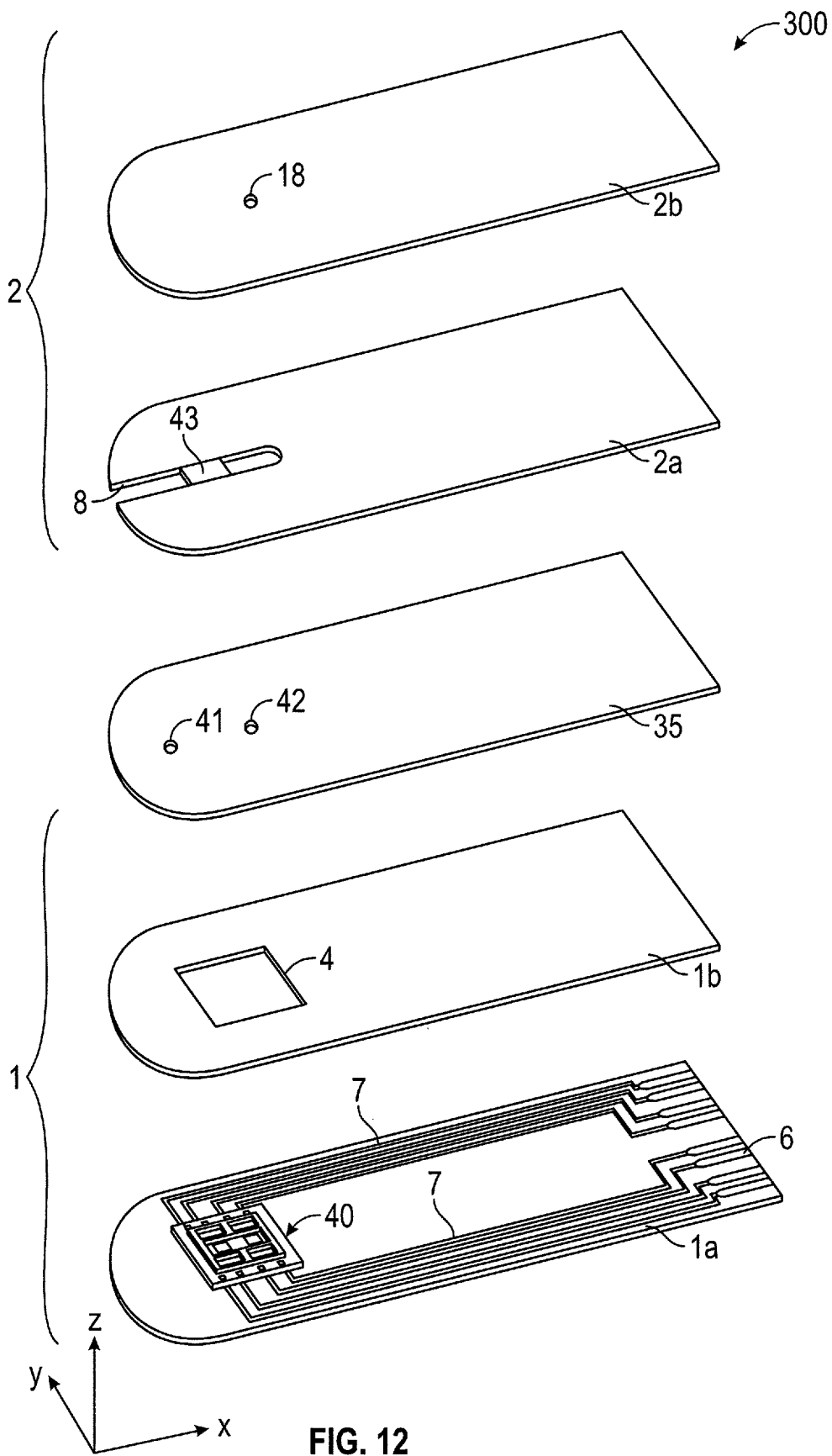
FIG. 12 is an exploded perspective view of a biosensor according to a third embodiment of the present invention.

The assisting board 35 is a board introduced between the first cover member 1 and second cover member 2 as illustrated in FIG. 12, and the outer shape and size thereof is the same as that of the second board 1b, for example. The thickness of the assisting board 35 is, for example, 0.1 mm to 0.5 mm. The assisting board 35 is applied to the second board 1b below and the third board 2a above, by way of adhesive agent or double-sided tape or the like.

The element-accommodating recess 5 for accommodating a detection element 40 is somewhat larger than the planar shape of the detection element 40, as described in the first embodiment as well. Accordingly, a gap is formed between the outer faces of the detection element 40 and the inner walls of the element-accommodating recess 5. The assisting board 35 serves to block off this gap. At the same time, the assisting board 35 also forms a part of the channel above the detection element 40.

Figure 13A:
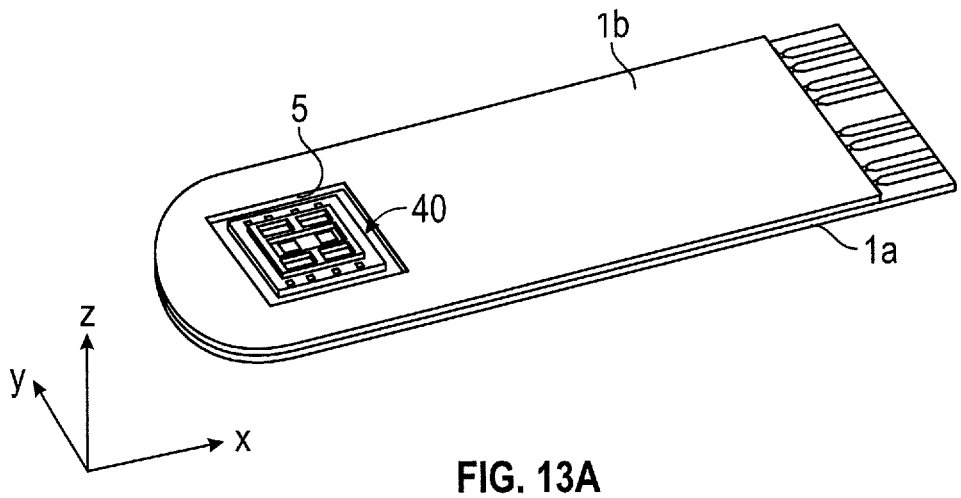
FIG. 13(a) is a perspective view of the biosensor illustrated in FIG. 12 in a state with the second cover member and an assisting board omitted.
Figure 13B:
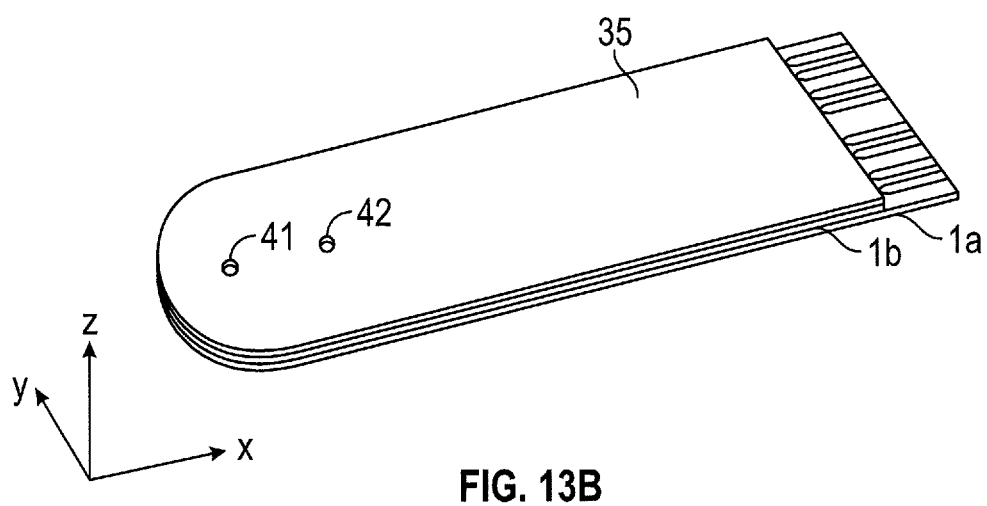
FIG. 13(b) is a perspective view of the biosensor illustrated in FIG. 12 in a state with the second cover member omitted.
Figure 13C:
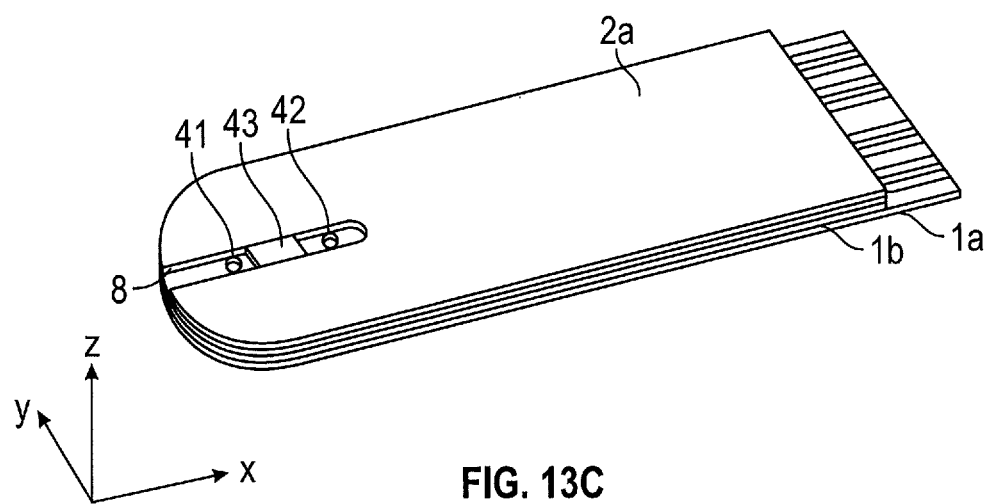
FIG. 13(c) is a perspective view of the biosensor illustrated in FIG. 12 in a state with the fourth board omitted.
Figure 14A:
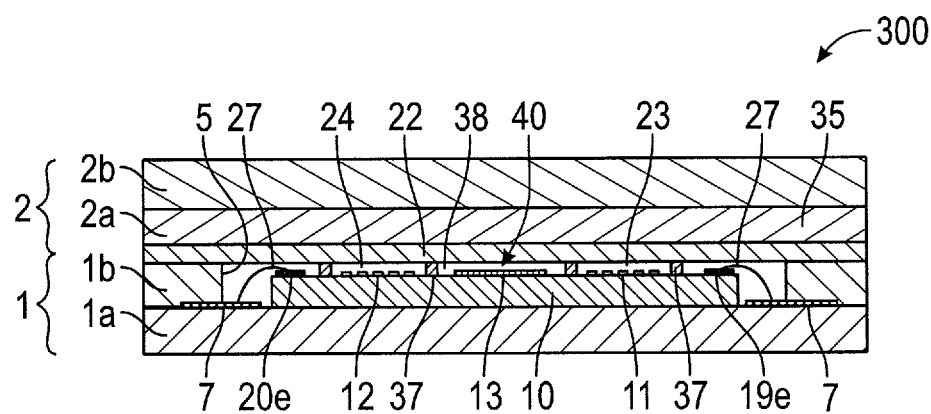
FIGS. 14(a) and 14(b) are cross-sectional views of the biosensor illustrated in FIG. 12, where
Figure 14B:
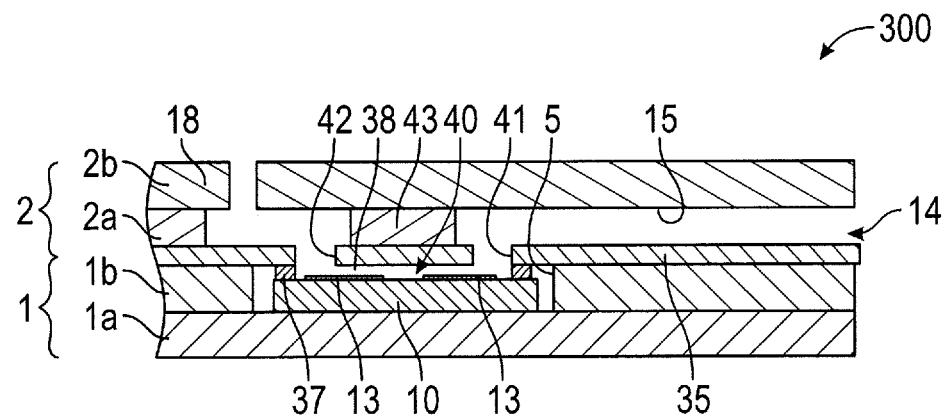

The way in which the assisting board 35 blocks the gap between the outer faces of the detection element 40 and the inner walls of the element-accommodating recess 5 while also forming the channel will be described with reference to FIG. 13 and FIG. 14. FIG. 13(a) through FIG. 13(c) are perspective views illustrating a state where certain members have been omitted from the biosensor 300. Specifically, FIG. 13(a) is a perspective view illustrating a state with the second cover member 2 and assisting board 35 omitted, FIG. 13(b) is a perspective view illustrating a state with the second cover member 2 omitted, and FIG. 13(c) is a perspective view illustrating a state with the fourth board 2b omitted. FIG. 14(a) is a cross-sectional view corresponding to FIG. 4(a), and FIG. 14(b) is a cross-sectional view corresponding to FIG. 4(b).

As illustrated in FIG. 13(a), a gap is formed in a state where the detection element 40 is accommodated in the element-accommodating recess 5, between the side faces of the detection element 40 and the inner walls of the element-accommodating recess 5. This gap is blocked off by the assisting board 35 layered on the second board 2b, as illustrated in FIG. 13(b).

Figure 15:
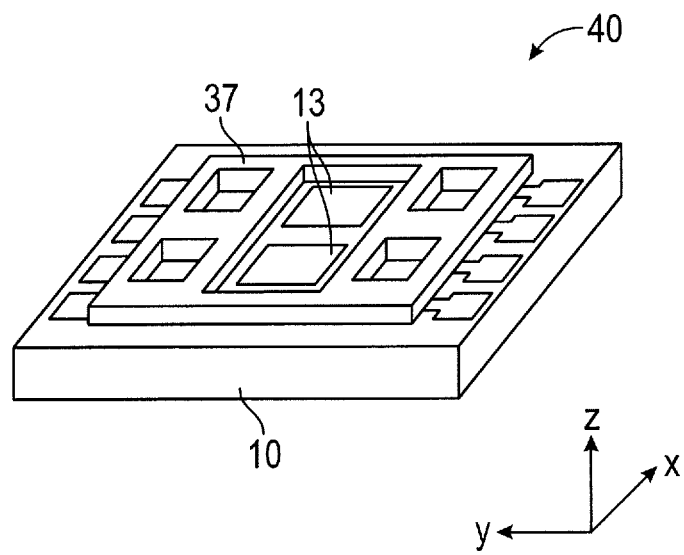
FIG. 15 is a perspective view of a detection element used in the biosensor illustrated in FIG. 12.

Now, the structure of the detection element 40 used in the biosensor 300 will be described. FIG. 15 is a perspective view of the detection element 40 used in the biosensor 300. The detection element 40 includes a frame member 37 disposed on the upper face of the element substrate 10. The frame member 37 includes a through hole at the middle portion to expose the two detection units 13, as well as through holes to expose the IDT electrodes. That is to say, the frame member 37 has a portion individually surrounding the detection units 13 and the IDT electrodes.

The portions serving as the frame of the frame member 37 are blocked by the assisting board 35, as illustrated in FIG. 14(a). Thus, the assisting board 35 functions as a lid to block the frame portions of the frame member 37, as well as serving to block the gap between the side faces of the detection element 40 and the inner walls of the element-accommodating recess 5. The first vibration space 23 is formed by the portions surrounding the first IDT electrodes 11 being blocked off, so the first IDT electrodes 11 are in a state of having been sealed within the first vibration space 23. In the same way, the second vibration space 24 is formed by the portions surrounding the second IDT electrodes 12 being blocked off, so the second IDT electrode 12 are in a state of having been sealed within the second vibration space 24. The portions surrounding the detection units 13 are also blocked off, with a space 38 formed at these portions.

The upper face of the frame member 37 is at the same position as the upper face of the second board 1b. In other words, the thickness of the frame member 37 is equal to the difference between the thickness of the second board 1b and the thickness of the element substrate 10. Forming the frame member 37 at this thickness enables the portions which are the frame of the frame member 37 to be blocked off, at the same time as blocking off the gap between the side faces of the detection element 40 and the inner walls of the element-accommodating recess 5. The thickness of the frame member 37 is 50 µm, for example.

Returning to FIG. 13(b), a first hole 41 and a second hole 42 are formed in the assisting board 35. These first hole 41 and second hole 42 both communicate with portions within the frame member 37 surrounding the detection units 13.

Thus, the third board 2a including the notch 8 is layered on the upper face of the assisting board 35 including the first hole 41 and second hole 42. The first hole 41 and second hole 42 are situated at positions over the notch 8 when the third board 2a is layered on the assisting board 35. The notch 8 serves as the groove 15, meaning that the groove 15 and space 38 are connected by the first hole 41 and second hole 42. The first hole 41 is formed closer to the opening side end of the notch 8 which will become the analyte solution inflow port, and the second hole 42 is formed farther away from the opening side end of the notch 8 as compared to the first hole 41. A partition 43 is formed at the portion between the first hole 41 and second hole 42. The planar shapes of the first hole 41 and second hole 42 may be optional shapes such as circular, rectangular, or the like. The shapes and sizes of the first hole 41 and second hole 42 may be the same or may be different.

The analyte solution channel in the biosensor 300 structured thus will be described with reference to the cross-sectional views in FIG. 14. When the inflow port 14 is brought into contact with the analyte solution, the analyte solution is suctioned by capillary action into the channel formed by the groove 15, as described in the first embodiment. Upon the analyte solution flowing therein reaching the first hole 41, the analyte solution enters the space 38 by the same capillary action via the first hole 41, so the space 38 is filled with the analyte solution. At this time, the air in the space 38 is vented from the second hole 42. Measurement regarding the analyte solution is performed in this state. Thus, the space 38 is a part of the channel in the biosensor 300. At least the surface of the assisting board 35 is hydrophilic, to facilitate capillary action. Formation of the partition 43 causes the analyte solution which has reached the partition 43 to be held back and to enter the space 38 via the first hole 41.

The space 38, first vibration space 23, and second vibration space 24, are spaces partitioned by the frame member 37 and assisting board 35 as illustrated in FIG. 14(a), so analyte solution which has flowed into the space 38 can be suppressed from flowing into the first vibration space 23 and second vibration space 24. Also, the gap between the side faces of the detection element 3 and the inner walls of the element-accommodating recess 5 is blocked off by the assisting board 35, so the analyte solution can be suppressed from flowing into that gap as well.

Thus, according to the biosensor 300, flow of analyte solution to unnecessary portions can be suppressed, so short-circuiting between the wiring 7 is suppressed. The amount of analyte solution flowing through the channel can also be made uniform.

Unlike the above-described embodiments, the wiring 7 of the biosensor 300 is disposed on the bottommost layer, which is the first board 1a. Accordingly, the fine metal wires 27 connecting the wiring 7 to the ends 19e and 20e of the first and second first extracting electrodes of the detection element 3 are inserted downwards from the upper face of the of the detection element 3, so the upward curving portion of the fine metal wires 27 is not very high. This facilitates situating the peak of the fine metal wires 27 at a position lower than the height of the frame member 37. Also, this does away with the need to perform separate work to prevent the fine metal wires 27 from coming into contact with the assisting board 35, so production efficiency improves. Note however, the position of the fine metal wire 27 is not restricted to this, and may be provided to the second board 1b in the same way as with the first embodiment, for example. In cases where the fine metal wires 27 will come into contact with the assisting board 35 if bonded in that state, the frame member 37 may be made thicker, or a through hole may be provided to the assisting board 35 at the region above the fine metal wires 27.

Figure 16:
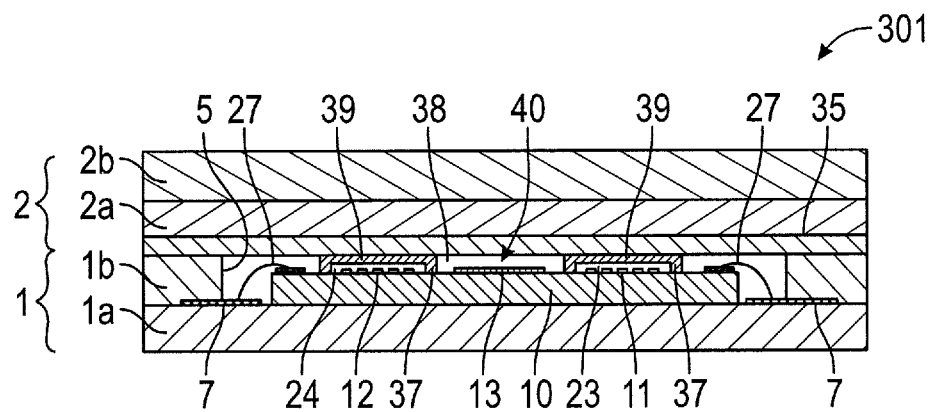
FIG. 16 is a cross-sectional view illustrating a modification of the biosensor illustrated in FIG. 12.

FIG. 16 is a cross-sectional view corresponding to FIG. 14(a), illustrating a modification 301 of the biosensor 300. While the assisting board 35 in the biosensor 300 described above also functions as a lid for the frame member 37, a second frame member 37b is provided separately from the assisting board 35 with this modification.

Figure 17:
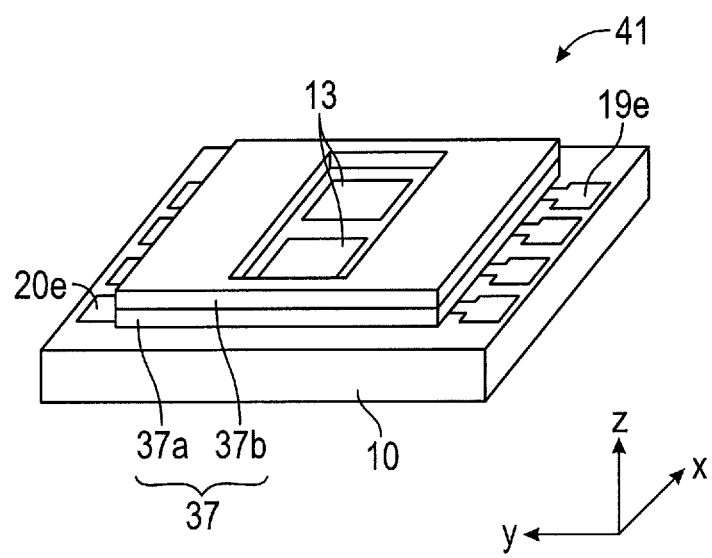
FIG. 17 is a perspective view of a detection element used in the biosensor illustrated in FIG. 16.

FIG. 17 illustrates a perspective view of a detection element 41 used in the modification 301. The detection element 41 differs from the detection element 40 illustrated in FIG. 15 with regard to the structure of the frame member 37. The frame member 37 of the modification 301 includes a first frame member 37a and second frame member 37b layered on the first frame member 37a. The structure of the first frame member 37a is the same as that of the frame member 37 of the biosensor 300, having portions surrounding the two detection units 13 and IDT electrodes. The external shape and size of the second frame member 37b is the same as that of the first frame member 37a in plan view, but through holes are not formed at portions corresponding to the first IDT electrodes 11 and second IDT electrodes 12. Accordingly, the portion surrounding the first IDT electrodes 11 is blocked off by the second frame member 37b so as to form the first vibration space 23, and the portion surrounding the second IDT electrodes 12 is blocked off by the second frame member 37b in the same way to form the second vibration space 24. On the other hand, a through hole which is the same shape and size of that in the first frame member 37a is formed in the second frame member 37b at the region directly above the detection units 13. This portion is blocked off by the assisting board 35 so as to form the space 38 serving as part of the channel.

Constructing the frame member 37 thus increases the area of contact between the assisting board 35 and frame member 37, so the assisting board 35 and a lid member 39 can be strongly bonded.

Fourth Embodiment

Next, a biosensor 400 according to a fourth embodiment will be described with reference to FIG. 18 through FIG. 20.

The biosensor 400 differs from the biosensor 100 according to the first embodiment described above, with regard to the point of including an assisting board 44.

Figure 18:
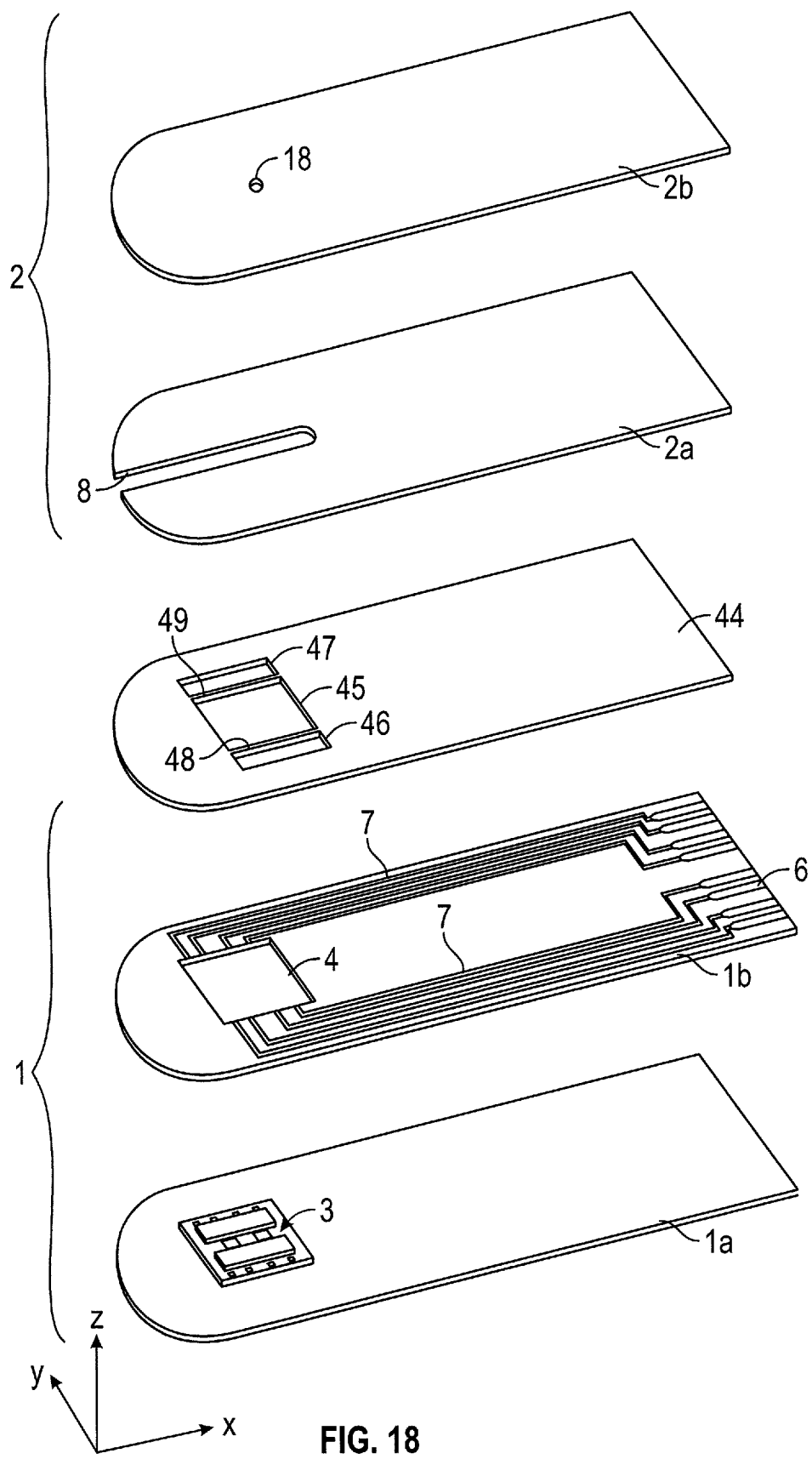
FIG. 18 is an exploded perspective view of a biosensor according to a fourth embodiment of the present invention.

The assisting board 44 is a board introduced between the first cover member 1 and second cover member 2 as illustrated in FIG. 18, and the outer shape and size thereof is the same as that of the third board 2a, for example. The thickness of the assisting board 44 is, for example, 0.1 mm to 0.5 mm. The assisting board 44 is applied to the second board 1b below and the third board 2a above, by way of adhesive agent or double-sided tape or the like. A hole portion 45 is formed in the assisting board 44 so that the detection units 13 of the detection element 3 are exposed when the assisting board 44 is layered on the first cover member 1. Situated on either side of the hole portion 45 are a third hole portion 45 and fourth through hole 46, having the same function as the first through hole 16 and second through hole 17 in the third board 2a of the biosensor 100 according to the first embodiment, as described later.

Figure 19A:
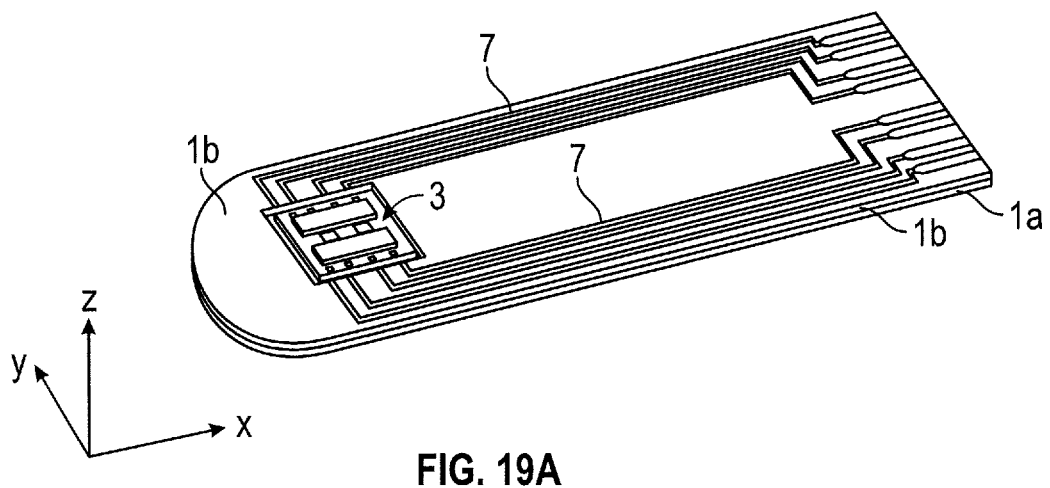
FIG. 19(a) is a perspective view of the biosensor illustrated in FIG. 18 in a state with the second cover member and assisting board omitted.
Figure 19B:
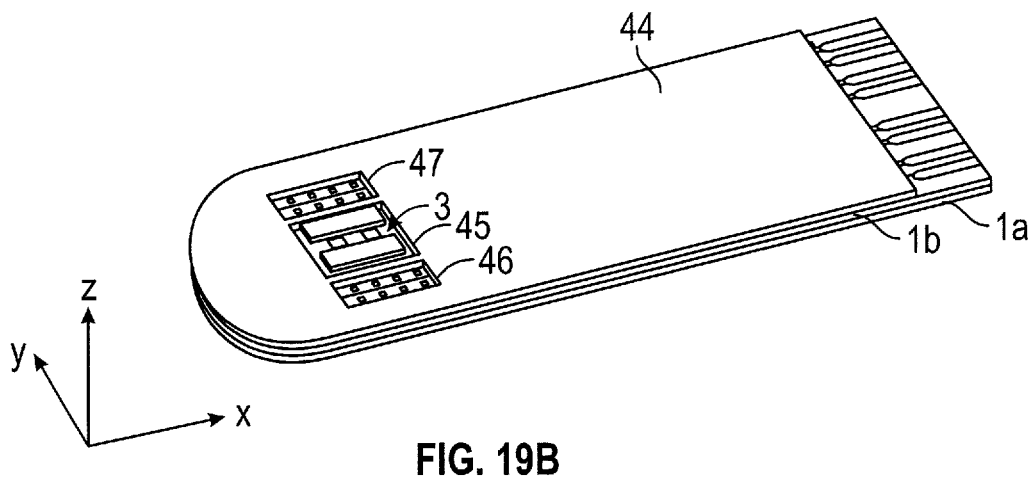
FIG. 19(b) is a perspective view of the biosensor illustrated in FIG. 18 in a state with the second cover member omitted.
Figure 19C:
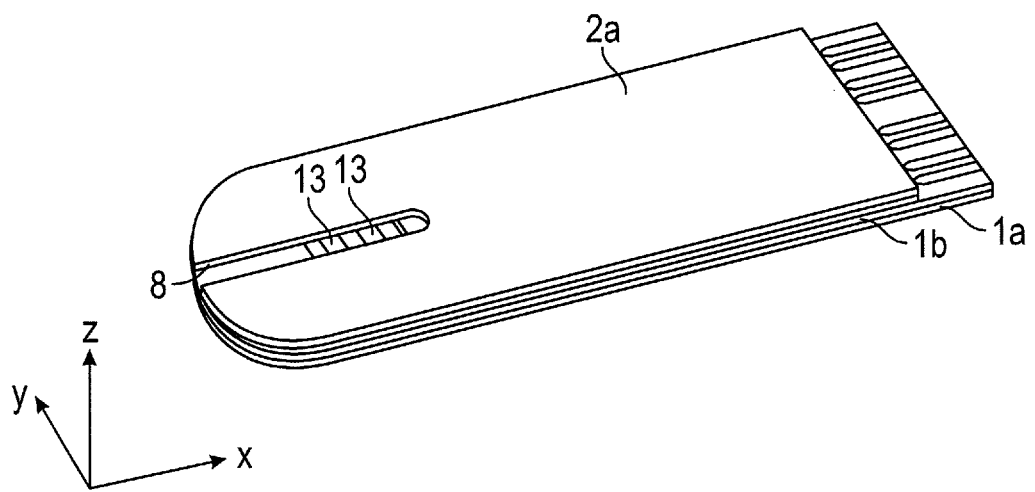
FIG. 19(c) is a perspective view of the biosensor illustrated in FIG. 18 in a state with a third board omitted.
Figure 20A:
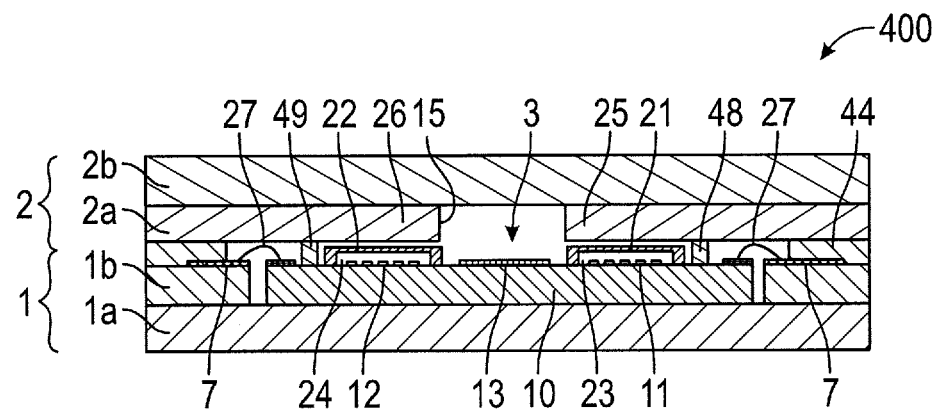
FIGS. 20(a) and 20(b) are cross-sectional views of the biosensor illustrated in FIG. 18, where
Figure 20B:
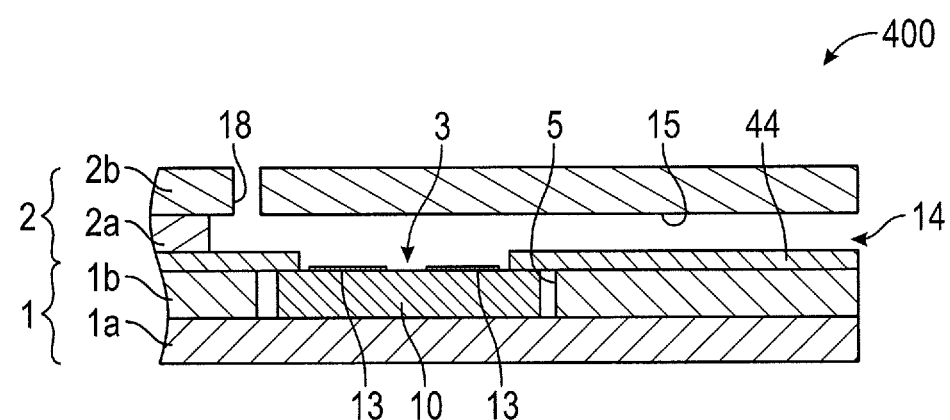

The assisting board 44 serves to isolate the analyte solution channel from the gap formed between the side faces of the detection element 3 and the inner walls of the element-accommodating recess 5. This will be described with reference to FIG. 19 and FIG. 20. FIG. 19(a) through FIG. 19(c) are perspective views illustrating a state where certain members have been omitted from the biosensor 400. Specifically, FIG. 19(a) is a perspective view illustrating a state with the second cover member 2 and assisting board 44 omitted, FIG. 19(b) is a perspective view illustrating a state with the second cover member 2 omitted, and FIG. 19(c) is a perspective view illustrating a state with the fourth board 2b of the second cover member 2 omitted. FIG. 20(a) is a cross-sectional view corresponding to FIG. 4(a), and FIG. 20(b) is a cross-sectional view corresponding to FIG. 4(b).

As illustrated in FIG. 19(a), a gap is formed in a state where the detection element 3 is accommodated in the element-accommodating recess 5, between the side faces of the detection element 3 and the inner walls of the element-accommodating recess 5. Layering the assisting board 44 thereupon exposes a part of the detection element 3 from the hole portion 45 in the assisting board 44, as illustrated in FIG. 19(b). The hole portion 45 is formed to a size such that the perimeter thereof is situated inwards from the perimeter of the detection element 3. Thus, of the gap formed between the side faces of the detection element 3 and the inner walls of the element-accommodating recess 5 of the biosensor 400, the gap portions situated at both ends in the x direction (gap portions following the y direction) are situated beneath the assisting board 44. That is to say, of the gap formed between the side faces of the detection element 3 and the inner walls of the element-accommodating recess 5, the gap portions situated at both ends in the x direction are blocked off. On the other hand, of the gap formed between the side faces of the detection element 3 and the inner walls of the element-accommodating recess 5 of the biosensor 400, the gap portions situated at both ends in the y direction (gap portions following the x direction) are exposed from the third through hole 46 and fourth through hole 47.

The third board 2a in which is formed the notch 8 is layered on the assisting board 44 layered on the first cover member 1. The hole portion 45 to expose the detection element 3 is formed to the assisting board 44, so the detection units 13 are exposed from the notch 8 in plan view in the state illustrated in FIG. 19(c).

The analyte solution channel in the biosensor 400 constructed thus is basically the same as that of the biosensor 100 according to the first embodiment, as illustrated by the cross-sectional views in FIG. 20. That is to say, when the inflow port 14 is brought into contact with the analyte solution, the analyte solution flows into the channel formed by the groove 15 by capillary action. The analyte solution which has flowed in reaches the detection units 13, and measurement is performed.

At this time, the portions of the gap formed between the side faces of the detection element 3 and the inner walls of the element-accommodating recess 5 that overlap the groove 15 are blocked by the assisting board 44 as illustrated in FIG. 20(b), so the analyte solution is kept from entering the gap. Also, the portions of the gap formed between the side faces of the detection element 3 and the inner walls of the element-accommodating recess 5 that are orthogonal to the groove 15 (gaps visible in FIG. 20(a)) are not blocked off by the assisting board 44, but the assisting board 44 can keep the analyte solution from entering these gaps. The reason is that the channel and gaps are partitioned by a third partition 48 which is the portion between the hole portion 45 and third through hole 46 of the assisting board 44, and a fourth partition 49 which is the portion between the hole portion 45 and fourth through hole 47 of the assisting board 44, as illustrated in FIG. 20(a).

Thus, according to the biosensor 400, flow of analyte solution to unnecessary portions can be suppressed, so short-circuiting between the wiring 7 is suppressed. Also, there is hardly any flow of analyte solution to unnecessary portions other than the channel, so the amount of analyte solution regarding which measurement is to be performed can be made uniform.

The present invention is not restricted to the above embodiments, and may be carried out in various modes.

In the above embodiments, description has been made regarding an arrangement where a detection unit 13 includes a metal film and an aptamer fixed to the surface of the metal film. However, in cases where the target matter in the analyte solution reacts with the metal film, the detection unit 13 may be configured including only the metal film, without using the aptamer. Further, an arrangement may be made where the metal film is not used, and the region between the first IDT electrodes 11 and second IDT electrodes 12 on the surface of the element substrate 10 which is a piezoelectric substrate is used as the detection unit 13. In this case, physical properties of the analyte solution such as viscosity is detected by directly applying the analyte solution to the surface of the element substrate 10. More specifically, change in the phase of SAWs due to the viscosity and so forth of the analyte solution on the detection unit 13 changing can be read.

Also, while description has been made in the above embodiments regarding an arrangement where the detection element 3 is a surface acoustic wave device, the detection element 3 is not restricted to this, and a detection element 3 in which has been formed an optical waveguide so that surface plasmon resonance occurs, may be used. In this case, change in refractive index of light or the like at the detection unit is read. Moreover, a detection element 3 including an oscillator formed on a piezoelectric substrate such as crystal, may be used. In this case, change in oscillation frequency of the oscillator is read.

Also, multiple types of devices may coexist on the same substrate for the detection element 3. For example, an enzyme electrode for the enzyme electrode method may be situated next to a SAW device. In this case, measurement according to the enzyme method is enabled in addition to the immunization method using antibodies or aptamers, increasing the number of items which can be tested at one time.

Also, while an example has been illustrated in the above embodiments where the first cover member 1 is formed of the first board 1a and second board 1b, and the second cover member 2 is formed of the third board 2a and fourth board 2b, the present invention is not restricted to this, and one of the boards may be integrated. For example, a first cover member 1 in which the first board 1a and second board 1b are integrally formed may be used.

Also, while an example has been illustrated in the above embodiments where one detection element 3 is provided, multiple detection elements 3 may be provided. In this case, one element-accommodating recess 5 may be formed for each detection element 3, or an elongated element-accommodating recess 5 may be formed to accommodate all of the detection elements 3.

Also, the modifications of biosensors and forms of the components described in the embodiments may be applied to biosensors according to other embodiments, such as applying a modification of the biosensor 100 according to the first embodiment to the biosensor 200 according to the second embodiment, without departing from the technical idea of the present invention.

REFERENCE SIGNS LIST 1 first cover member
2 second cover member
3 detection element
4 recess-forming through hole
5 element-accommodating recess
8 notch
10 element substrate
11 first IDT electrode
12 second IDT electrode
13 detection unit
14 inflow port
15 groove
16 first through hole
17 second through hole
18 vent hole
19 first extracting electrode
20 second extracting electrode
21 first protective member
22 second protective member
23 first vibration space
24 second vibration space
31 mounting member
35 assisting board

The invention claimed is:

1. A biosensor, comprising:
a first cover member comprising an element-accommodating recess in an upper face thereof;
a detection element using a surface acoustic wave, the detection element comprising an element substrate accommodated in the element-accommodating recess, and at least one detection unit located on an upper face of the element substrate configured to perform detection of an analyte, wherein the detection element further comprises a first electrode and a second electrode;
a second cover member joined to the first cover member and covering the detection element, and comprising an inflow port from which the analyte flows in and a groove which extends from the inflow port to at least above the at least one detection unit; and
a first protective member and a second protective member located on the upper face of the element substrate, wherein the first electrode is located within the first protective member and the second electrode is located within the second protective member, and wherein an upper face of the detection element is located below an upper face of at least one of the first protective member and the second protective member.

2. The biosensor according to claim 1, wherein a gap exists between a side face of the detection element and inner walls of the element-accommodating recess.

3. The biosensor according to claim 2, wherein a height of the upper face of the element substrate from a bottom face of the element-accommodating recess is equal to or lower than a depth of the element-accommodating recess.

4. The biosensor according to claim 1, wherein
the groove extends from the inflow port toward the at least one detection unit past the at least one detection unit, and
the second cover member further comprises a vent hole connected to the groove.

5. The biosensor according to claim 1, wherein
the first cover member comprises a first board with a flat shape, and a second board joined to an upper face of the first board and comprising a recess-forming through hole, and
a bottom face of the element-accommodating recess is the upper face of the first board, and inner walls of the element-accommodating recess are inner walls of the recess-forming through hole.

6. The biosensor according to claim 1, wherein
the second cover member comprises a third board with a flat shape comprising a notch which penetrates in a thickness direction of the third board, and a fourth plate with a flat shape joined to an upper face of the third board, and
a bottom face of the groove is a lower face of the fourth board located above the notch, and inner walls of the groove are inner walls of the notch.

7. The biosensor according to claim 6, wherein
the detection element further comprises:
the first electrode comprises a first interdigital transducer (IDT electrode located on the upper face of the element substrate configured to generate elastic waves to be propagated toward the at least one detection unit,
the second electrode comprises a second IDT electrode located on the upper face of the element substrate configured to receive the elastic waves passing through the at least one detection unit,
the first protective member comprises a first recess and seals the first IDT electrode within a first vibration space surrounded by inner faces of the first recess and the upper face of the element substrate, and
the second protective member comprises a second recess and seals the second IDT electrode within a second vibration space surrounded by inner faces of the second recess and the upper face of the element substrate,
a first extracting electrode led out from the first IDT electrode in an opposite direction of a side of the at least one detection unit, and comprises an end located on an outer side of the first protective member, and
a second extracting electrode led out from the second IDT electrode in an opposite direction of a side of the at least one detection unit, and comprises an end located on an outer side of the second protective member, the third board further comprises a first through hole and a second through hole on both sides of the notch, in a direction orthogonal to the direction in which the notch extends, the first through hole being located on the first extracting electrode and the second through hole being located on the second extracting electrode, and
a first partition, which is a portion between the notch and the first through hole of the third board, is located above the first protective member, and a second partition, which is a portion between the notch and the second through hole of the third board, is located above the second protective member.

8. The biosensor according to claim 7, wherein the first partition is located above the first protective member with a gap therebetween, and the second partition is located above the second protective member with a gap therebetween.

9. The biosensor according to claim 8, further comprising:
a first insulating member covering a portion of the first extracting electrode located outside of the first protective member; and
a second insulating member covering a portion of the second extracting electrode located outside of the second protective member.

10. The biosensor according to claim 1, wherein:
the first electrode comprises a first interdigital transducer (IDT) electrode located on the upper face of the element substrate configured to generate elastic waves to be propagated toward the at least one detection unit,
the second electrode comprises a second IDT electrode located on the upper face of the element substrate configured to receive the elastic waves passing through the at least one detection unit,
the first protective member comprises a first recess and seals the first IDT electrode within a first vibration space surrounded by inner faces of the first recess and the upper face of the element substrate, and
the second protective member comprises a second recess and seals the second IDT electrode within a second vibration space surrounded by inner faces of the second recess and the upper face of the element substrate.

11. The biosensor according to claim 10, wherein the detection element further comprises
a first extracting electrode led out from the first IDT electrode in an opposite direction of a side of the at least one detection unit, and comprises an end located on an outer side of the first protective member, and
a second extracting electrode led out from the second IDT electrode in an opposite direction of a side of the at least one detection unit, and comprises an end located on an outer side of the second protective member.

12. The biosensor according to claim 1, wherein
the detection element comprises a plurality of detection units, and
the plurality of detection units is arranged along a direction in which the groove extends.

13. The biosensor according to claim 1, further comprising an assisting board introduced between the first cover member and the second cover member,
wherein the detection element further comprises a frame member located on the upper face of the element substrate and surrounding the at least one detection unit, and
wherein the assisting board blocks off a portion of the frame member surrounding the at least one detection unit and a gap between side faces of the at least one detection unit and inner walls of the element-accommodating recess, and comprises a first hole portion connecting from the groove to inside a frame of the frame member surrounding the at least one detection unit.

14. The biosensor according to claim 13, wherein the assisting board further comprises a second hole portion connecting from the groove to inside the frame of the frame member surrounding the at least one detection unit, and the first hole portion is located closer to the inflow port than the second hole portion.

15. The biosensor according to claim 1, further comprising an assisting board between the first cover member and the second cover member, wherein the assisting board comprises a hole portion at a region overlapping with the element substrate, and wherein inner walls of the hole portion are located further inside than a perimeter of the upper face of the element substrate in plan view.

16. A biosensor, comprising:

a cover member comprising an inflow port for an analyte, a groove-shaped channel connected to the inflow port and constituting a capillary, and a recessed space connected to the channel; and a detection element using a surface acoustic wave, the detection element comprising an element substrate accommodated in the space, and a detection unit which is located on an upper face of the element substrate and reacts with a component included in the analyte, wherein the cover member further comprises:

a first board with a flat shape, and a second board joined to an upper face of the first board and comprising a recess-forming through hole, and a bottom face of the element-accommodating recess is the upper face of the first board, and inner walls of the element-accommodating recess are inner walls of the recess-forming through hole.

17. The biosensor according to claim 16, wherein inner faces of the channel are hydrophilic.

* * * * *